(12) United States Patent
Cheng et al.

(10) Patent No.: US 6,316,464 B1
(45) Date of Patent: Nov. 13, 2001

(54) P38 MAP KINASE INHIBITORS

(75) Inventors: Soan Cheng, San Diego; David Michael Goldstein, San Jose; Teresa Alejandra Trejo Martin, Palo Alto; Eric Brian Sjogren, Mountain View, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/174,299

(22) Filed: Oct. 16, 1998

Related U.S. Application Data

(60) Provisional application No. 60/062,548, filed on Oct. 20, 1997, provisional application No. 60/075,515, filed on Feb. 20, 1998, and provisional application No. 60/096,916, filed on Oct. 18, 1998.

(51) Int. Cl.[7] .................................................. A01N 43/42
(52) U.S. Cl. ...................... 514/300; 544/350; 546/113; 546/115
(58) Field of Search .................... 546/113, 110; 514/300

(56) References Cited

U.S. PATENT DOCUMENTS

| | | |
|---|---|---|
| 3,888,851 | 6/1975 | Narr et al. . |
| 5,236,925 | 8/1993 | Primeau et al. . |
| 5,338,849 | 8/1994 | Festal et al. . |
| 5,502,187 | 3/1996 | Ayer et al. . |
| 5,521,213 | 5/1996 | Prasit et al. . |
| 5,589,482 | 12/1996 | Thompson . |

FOREIGN PATENT DOCUMENTS

| | | |
|---|---|---|
| 4304650 A1 | 8/1994 | (DE) . |
| 0 300688 A1 | 1/1989 | (EP) . |
| 0 655439 A2 | 5/1995 | (EP) . |
| 0 668279 A2 | 8/1995 | (EP) . |
| 0 737685 A1 | 10/1996 | (EP) . |
| 2 298 199 A | 8/1996 | (GB) . |
| 56104870 | 8/1981 | (JP) . |
| 371228 | 11/1973 | (SU) . |
| WO95/10513 A1 | 4/1995 | (WO) . |
| WO95/33748 A1 | 12/1995 | (WO) . |
| WO95/33752 A1 | 12/1995 | (WO) . |
| WO97/49706 A1 | 12/1997 | (WO) . |
| WO98/22457 A1 | 5/1998 | (WO) . |
| WO98/47899 A1 | 10/1998 | (WO) . |

OTHER PUBLICATIONS

Kelly J Chem Soc (C) 303–7, 1973.*
Clark et al., *Chemistry and Industry*, vol. 5: pp. 215–216, 1975, "Preparation of pyrrolo [2,3–p]pyrazines and pyrazino [2,3–p]indole".
Henry, et la., *J. Med. Chem.*, vol. 41, pp. 4196–4198, 1998, "6–Amino–2–(4–fluorophenyl)–4–methoxy–3–(4–pyridyl)–1H–pyrrolo[,3–b]pyridine (RWJ 68354): A Potent and Selective p38 Kinase Inhibitor".
Henry, et al., *Bioorg. Med. Chem. Lett.*, vol. 8:23, pp. 3335–40, 1998, "Potent Inhibitors of the Map Kinase p38".

* cited by examiner

*Primary Examiner*—Robert Gerstl
(74) *Attorney, Agent, or Firm*—Rekha Bansal; Rohan Peries

(57) ABSTRACT

The present invention relates to compounds of Formula (I)

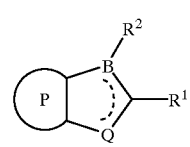

(I)

that are p-38 MAP kinase inhibitors, pharmaceutical compositions containing them, methods for their use, and methods for preparing these compounds.

21 Claims, No Drawings

P38 MAP KINASE INHIBITORS

CROSS-REFERENCE TO RELATED APPLICATIONS

This application claims the benefit under 35 U.S.C. 119(e) of U.S. Provisional Applications Ser. No. 60/062,548 filed Oct. 20, 1997, Ser. No. 60/075,515 filed Feb. 20, 1998 and Ser. No. 60/096,916 filed Aug. 18, 1998.

FIELD OF THE INVENTION

This invention relates to compounds that inhibit p38 MAP kinase, pharmaceutical compositions containing them, methods for their use, and methods for preparing these compounds.

BACKGROUND INFORMATION AND RELATED DISCLOSURES

TNF and IL-1 have been shown to be central players in the pathological processes underlying many chronic inflammatory and autoimmune diseases. IL-1 is implicated in mediating or exacerbating diseases such as rheumatoid arthritis ((see., Arend, W. P. *Arthritis & Rheumatism* 38(2): 151–160, (1995)), osteoarthritis, bone resorption, toxic shock syndrome, tuberculosis, atherosclerosis, diabetes, Hodgkin's disease (see., Benharroch, D.; et. al. *Euro. Cytokine Network* 7(1): 51–57) and Alzheimer's disease. Excessive or unregulated TNF production has been implicated in mediating or exacerbating diseases such as rheumatoid arthritis ((see., Maini, R. N.; et. al. *APMIS.* 105(4): 257–263, (1997); Feldmann, M., *J. of the Royal College of Physicians of London* 30(6): 560–570, (1996); Lorenz, H. M.; et. al. *J. of Immunology* 156(4): 1646–1653, (1996)) osteoarthritis, spondylitis, sepsis, septic shock ((see., Abraham, E.; et. al. *JAMA.* 277(19):1531–1538, (1997), adult respiratory distress syndrome, asthma ((see., Shah, A.; et. al. *Clin. & Exp. Allergy* 1038–1044, (1995) and Lassalle, P., et. al. *Clin. & Exp. Immunol.* 94(1): 105–110, (1993)), bone resorption diseases, fever ((see., Cooper, A. L., et. al. *Am. J. of Physiology* 267(6 Pt. 2): 1431–1436)), encephalomyelitis, demyelination ((see., Klindert, W. E.; et al. *J. of Neuroimmunol.* 72(2): 163–168, (1997)) and periodontal diseases.

Clinical trials with IL-1 and TNF receptor antagonists have shown that blocking the ability of these cytokines to signal through their receptors leads to significant improvement, in humans, in inflammatory diseases. Therefore, modulation of these inflammatory cytokines is considered one of the most effective strategies to block chronic inflammation and have positive therapeutic outcomes.

It has also been shown that p38 MAP kinase plays an important role in the translational control of TNF and IL-1 and is also involved in the biochemical signaling of these molecules ((see., Lee, J. C., et al. *Nature* 372 (6508): 739–46, (1994)). Compounds that bind to p38 MAP are effective in inhibiting bone resorption, inflammation, and other immune and inflammation-based pathologies. The characterization of the p38 MAP kinase and its central role in the biosynthesis of TNF and IL-1 have made this kinase an attractive target for the treatment of diseases mediated by these cytokines.

It would therefore be desirable to provide p38 MAP kinase inhibitors and thereby provide a means of combating diseases mediated by pro-inflammatory cytokines such as ITNF and IL-1. This invention fulfills this and related needs.

SUMMARY OF THE INVENTION

In a first aspect, this invention provides compounds selected from the group of compounds represented by Formula (I):

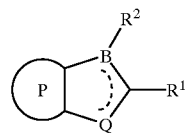

(I)

wherein:
   $R^1$ is heteroaryl;
   - - - - - - represents a bond between either B and $CR^1$ or Q and $CR^1$ such that:
   (i) when - - - - - - is between Q and —$CR^1$— then:
      B is nitrogen;
      $R^2$ is aryl; and
      Q is —CR— wherein:
         R is hydrogen, alkyl, haloalkyl, cycloalkyl, cycloalkylalkyl, heteroalkyl, acyl, heterocyclyl, heterocyclylalkyl, heterocyclylcarbonyl, nitro, cyano, amino, monosubstituted amino, disubstituted amino, acylamino, sulfonylamino, —$OR^5$ (where $R^5$ is hydrogen, alkyl, heteroalkyl or heterocyclylalkyl), —$COOR^7$ (where $R^7$ is hydrogen or alkyl) or —CONR'R" (where R' and R" independently represent hydrogen, alkyl or heteroalkyl); and
   (ii) when - - - - - - is between B and —$CR^1$— then:
      B is carbon;
      $R^2$ is aryl or heteroaryl; and
      Q is —$NR^4$—, —O—, or —S— wherein:
         $R^4$ is hydrogen, alkyl, alkenyl, alkynyl, haloalkyl, cycloalkyl, cycloalkylalkyl, heteroalkyl, acyl, aralkyl, heteroaralkyl, heterocyclyl, heterocyclylalkyl, heterocyclylcarbonyl, —$OR^5$ (where $R^5$ is hydrogen, alkyl, heteroalkyl or heterocyclylalkyl), —$SO_2R"$ (where R" is alkyl, amino, monosubstituted amino or disubstituted amino), —CONR'R" (where R' and R" independently represent hydrogen, alkyl or heteroalkyl), -(alkylene)-Z or -(alkylene)-CO-(alkylene)-Z wherein:
   Z is cyano;
      —$COOR^7$ where $R^7$ is hydrogen or alkyl;
      —$CONR^8R^9$ where $R^8$ is hydrogen or alkyl, $R^9$ is alkoxy or -(alkylene)-$COOR^7$, or $R^8$ and $R^9$ together with the nitrogen atom to which they are attached form a heterocycle;
      —C(=$NR^{10}$)($NR^{11}R^{12}$) where $R^{10}$, $R^{11}$ and $R^{12}$ independently represent hydrogen or alkyl, or $R^{10}$ and $R^{11}$ together are —$(CH_2)_n$— where n is 2 or 3 and $R^{12}$ is hydrogen or alkyl; or
      —$COR^{13}$ where $R^{13}$ is alkyl, heteroalkyl, heterocyclylalkyl, aryl, aralkyl, heteroaryl or heteroaralkyl; and

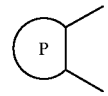

is a group represented by formula (S), (T), (U), (V) or (W);

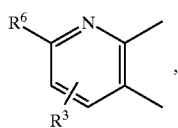
(S)

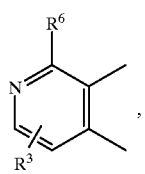
(T)

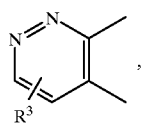
(U)

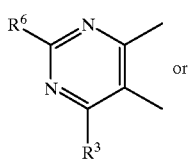
(V)

or

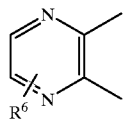
(W)

where:
R$^6$ is hydrogen, alkyl, heteroalkyl, heterocyclylalkyl, halo, cyano, nitro, amino, monosubstituted amino, disubstituted amino, —COOR$^{14}$, -(alkylene)-COOR$^{14}$ (where R$^{14}$ is hydrogen or alkyl), —CONR$^{15}$R$^{16}$ (where R$^{15}$ and R$^{16}$ independently represent hydrogen or alkyl, or R$^{15}$ and R$^{16}$ together with the nitrogen atom to which they are attached form a heterocycle), —S(O)$_n$R$^{17}$ (where n is an integer from 0 to 2 and R$^{17}$ is alkyl, amino, monosubstituted amino or disubstituted amino), —OR$^{18}$ (where R$^{18}$ is hydrogen, alkyl, heteroalkyl or heterocyclylalkyl), —NRC(O)R" [where R is hydrogen, alkyl or hydroxyalkyl and R" is hydrogen, alkyl, cycloalkyl or -(alkylene)-X where X is hydroxy, alkoxy, amino, alkylamino, dialkylamino, heterocyclyl or —S(O)$_n$R' (where n is 0 to 2 and R' is alkyl)], —NRSO$_2$R" [where R is hydrogen or alkyl and R" is alkyl or -(alkylene)-X where X is hydroxy, alkoxy, amino, alkylamino, dialkylamino or —S(O)$_n$R' (where n is 0 to 2 and R' is alkyl)]; and R$^3$ is hydrogen, alkyl, alkenyl, alkynyl, haloalkyl, heteroalkyl, cycloalkyl, cycloalkylalkyl, cycloalkylthio, aralkyl, heteroaralkyl, heterocyclyl, heterocyclylalkyl, halo, cyano, nitro, amino, monosubstituted amino, disubstituted amino, acylamino, sulfonylamino, —OR$^{19}$ (where R$^{19}$ is hydrogen, alkyl, heteroalkyl or heterocyclylalkyl), —COOR$^{20}$ (where R$^{20}$ is hydrogen or alkyl), —CONR$^{21}$R$^{22}$ (where R$^{21}$ and R$^{22}$ independently represent hydrogen, alkyl or heteroalkyl, or R$^{21}$ and R$^{22}$ together with the nitrogen atom to which they are attached form a heterocycle), —S(O)$_n$R$^{23}$ (where n is an integer from 0 to 2 and R$^{23}$ is alkyl, heteroalkyl, amino, monosubstituted amino or disubstituted amino), -(alkylene)-Z" or -(alkylene)-CO-(alkylene)-Z' wherein:
Z" is cyano;
—COOR$^{24}$ where R$^{24}$ is hydrogen or alkyl;
—CONR$^{25}$R$^{26}$ where R$^{25}$ and R$^{26}$ independently represent hydrogen or alkyl, or R$^{25}$ and R$^{26}$ together with the nitrogen atom to which they are attached form a heterocycle;
—C(=NR$^{27}$)(NR$^{28}$R$^{29}$) where R$^{27}$, R$^{28}$ and R$^{29}$ independently represent hydrogen or alkyl, or R$^{27}$ and R$^{28}$ together are —(CH$_2$)$_n$— where n is 2 or 3 and R$^{29}$ is hydrogen or alkyl; or
—COR$^{30}$ where R$^{30}$ is alkyl, heteroalkyl, heterocyclylalkyl, aryl, aralkyl, heteroaryl or heteroaralkyl; and their pharmaceutically acceptable salts, prodrugs, individual isomers, and mixtures of isomers, provided that both R$^3$ and R$^6$ are not either amino, monosubstituted amino or disubstituted amino.

In a second aspect, this invention provides compounds selected from the group of compounds represented by Formula (IIa):

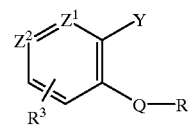
(IIa)

wherein:
One of Z$^1$ and Z$^2$ is nitrogen and the other is —CR$^6$— wherein R$^6$ is hydrogen, alkyl, or alkoxy; or both Z$^1$ and Z$^2$ are nitrogen such that:
(a) when Z$^1$ or Z$^2$ is nitrogen and the other is —CR$^6$— then:
(i) when Y is halo, then —Q—R is —NH—C(R$^1$)=CH(R$^2$) or —N=C(CH$_3$)(R$^1$);
(ii) when Y is —C(R$^2$)=C(R$^1$)OX (where X is p-CH$_3$C$_6$H$_4$SO$_2$—, CH$_3$SO$_2$—, or CF$_3$SO$_2$—), then —Q—R is nitro or amino; and
(iii) when Y is —C(O)R$^2$, then —Q—R is —NHC(O)R$^1$, —OCH$_2$CO$_2$R, or —SCH$_2$R$^1$ where:
R is alkyl;
R$^1$ is heteroaryl; and
R$^2$ is aryl or heteroaryl; and
(b) when Z$^1$ and Z$^2$ both are nitrogen then:
Y is halo and —Q—R is —NH—C(R$^1$)=CH(R$^2$) where R$^1$ and R$^2$ are as defined above; and
R$^3$ is hydrogen, alkyl, halo, or alkoxy.

In a third aspect, this invention provides compounds selected from the group of compounds represented by Formula (IIb):

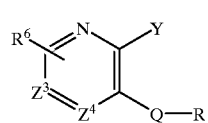
(IIb)

wherein:
Z$^3$ is nitrogen and Z$^4$ is —CR$^3$— wherein R$^3$ is hydrogen, alkyl, or alkoxy; or Z$^4$ is nitrogen and Z$^3$ is —CH—; such that:

(a) when Y is hydrogen, then —Q—R is —NH—N=C(R¹)CH₂(R²); and
(b) when Y is —C(O)R², then —Q—R is —OCH₂CO₂R or —SCH₂R¹ where:
R is alkyl;
R¹ is heteroaryl; and
R² is aryl or heteroaryl; and
R⁶ is hydrogen, alkyl, halo, or alkoxy.

In a fourth aspect, this invention provides pharmaceutical compositions containing a therapeutically effective amount of a compound of Formula (I) or its pharmaceutically acceptable salt and a pharmaceutically acceptable excipient.

In a fifth aspect, this invention provides a method of treatment of a disease in a mammal treatable by administration of a p38 MAP kinase inhibitor, comprising administration of a therapeutically effective amount of a compound of Formula (I) or its pharmaceutically acceptable salt.

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, pentyl, and the like.

"Cycloalkyl" means a saturated monovalent cyclic hydrocarbon radical of three to six ring carbons, e.g., cyclopropyl, cyclohexyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkenylene" means a linear divalent hydrocarbon radical of two to six carbon atoms or a branched divalent hydrocarbon radical of three to six carbon atoms, containing at least one double bond, e.g., ethenylene, propenylene, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkoxy" means a radical —OR where R is alkyl as defined above, e.g., methoxy, ethoxy, propoxy, 2-propoxy, the like.

"Acyl" means a radical —C(O)R where R is hydrogen, alkyl, alkenyl, cycloalkyl, heteroalkyl, haloalkyl, aryl, aralkyl, heteroaryl or heteroaralkyl, e.g., acetyl, benzoyl, thenoyl, and the like.

"Acyloxy" means a radical —OC(O)R where R is hydrogen, alkyl, alkenyl, cycloalkyl, haloalkyl, heterocyclyl or —NRR' (where R and R' are independently of each other hydrogen or alkyl), e.g., acetoxy, and the like.

"Acylamino" means a radical —NRC(O)R' where R is hydrogen or alkyl and R' is hydrogen, alkyl, alkenyl, cycloalkyl, heteroalkyl, haloalkyl, aryl, aralkyl, heteroaryl or heteroaralkyl, e.g., acetylamino, trifluoroacetylamino, benzoylamino, methylacetylamino, and the like.

"Sulfonylamino" means a radical —NRSO₂R' where R is hydrogen or alkyl and R' is hydrogen, alkyl, alkenyl, cycloalkyl, heteroalkyl, haloalkyl, amino, monosubstituted amino, disubstituted amino, aryl, aralkyl, heteroaryl or heteroaralkyl, e.g., methylsulfonylamino, benzylsulfonylamino, phenylsulfonylamino, and the like.

"Halo" means fluoro, chloro, bromo, or iodo, preferably fluoro and chloro.

"Haloalkyl" means alkyl substituted with one or more same or different halo atoms, e.g., —CH₂Cl, —CF₃, —CH₂CF₃, —CH₂CCl₃, and the like.

"Monosubstituted amino" means a radical —NHR where R is alkyl, alkenyl, heteroalkyl, haloalkyl, heterocyclylalkyl, cycloalkyl, cycloalkylalkyl, aryl, aralkyl, heteroaryl, heteroaralkyl or an amino protecting group, e.g., methylamino, (1-methylethyl)amino, phenylamino, and the like.

"Disubstituted amino" means a radical —NRR' where R and R' are independently alkyl, alkenyl, heteroalkyl, haloalkyl, heterocyclylalkyl, cycloalkyl, cycloalkylalkyl, aryl, aralkyl, heteroaryl or heteroaralkyl. Representative examples include, but are not limited to, dimethylamino, methylethylamino, di(1-methylethyl)amino, methylbenzylamino, and the like.

"Aryl" means a monovalent monocyclic or bicyclic aromatic hydrocarbon radical of 6 to 10 ring atoms, and optionally substituted independently with one, two or three substituents selected from alkyl, haloalkyl, heteroalkyl, heterocyclylalkyl, cycloalkyl, cycloalkylalkyl, halo, nitro, cyano, acyloxy, optionally substituted phenyl, heteroaryl, heteroaralkyl, —COR (where R is alkyl, haloalkyl, cycloalkyl or cycloalkylalkyl), —NRR' (where R and R' are, independently of each other, hydrogen, alkyl or heteroalkyl), —OR (where R is hydrogen, alkyl, haloalkyl, cycloalkyl, cycloalkylalkyl, heteroalkyl or optionally substituted phenyl), —NRC(O)R (where R is hydrogen or alkyl and R' is alkyl, haloalkyl, cycloalkyl or cycloalkylalkyl), —COOR, —(alkenylene)-COOR, -(alkylene)-COOR (where R is hydrogen or alkyl), —CONR'R" and —(alkylene)-CONR'R" (where R' and R" are independently selected from hydrogen, alkyl, cycloalkyl or cycloalkylalkyl). More specifically the term aryl includes, but is not limited to, phenyl, 1-naphthyl, 2-naphthyl, and derivatives thereof.

"Optionally substituted phenyl" means a phenyl group which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heteroaryl" means a monovalent monocyclic or bicyclic aromatic radical of 5 to 10 ring atoms containing one, two or three ring heteroatoms selected from N, O, or S, the remaining ring atoms being C. The aromatic radical is optionally substituted independently with one, two or three substituents selected from alkyl, haloalkyl, cycloalkyl, cycloalkylalkyl, cyanoalkyl, hydroxylamino, heteroalkyl, halo, nitro, cyano, heterocyclylalkyl, optionally substituted phenyl, —COR (where R is alkyl, haloalkyl, cycloalkyl or cycloalkylalkyl), —NRR [where R and R' are independently of each other hydrogen, alkyl, cycloalkyl, cyanoalkyl, carboxyalkyl, alkoxycarbonylalkyl, heteroalkyl, heterocyclylalkyl, -(alkylene)-CO—Z (where Z is amino, alkylamino, or dialkylamino) or optionally substituted phenyl], —OR (where R is hydrogen, alkyl, haloalkyl, alkenyl, cycloalkyl, cycloalkylalkyl, cyanoalkyl, carboxyalkyl, alkoxycarbonylalkyl, heteroalkyl, heterocyclylalkyl or optionally substituted phenyl), —NRS$_2$R" [where R is hydrogen or alkyl and R" is alkyl or -(alkylene)-X where X is hydroxy, alkoxy, amino, alkylamino, dialkylamino or —S(O)$_n$R' (where n is 0 to 2 and R' is alkyl)], —NR$^a$C(O)R$^b$ [where R$^a$ is hydrogen or alkyl and R$^b$ is hydrogen, alkyl, -(alkylene)-X where X is hydroxy, alkoxy, amino, alkylamino, dialkylamino, cycloalkyl, heterocyclyl, optionally substituted phenyl, optionally substituted heteroaryl ring or —S(O)$_n$R' (where n is 0 to 2 and R' is alkyl)], —S(O)$_n$R (where n is an integer from 0 to 2 and R is hydrogen, alkyl, haloalkyl, alkenyl, cycloalkyl or cycloalkylalkyl), —SO$_2$NRR' (where R and R' are independently of each other hydrogen, alkyl cyanoalkyl, carboxyalkyl, alkoxycarbonylalkyl, hydroxyalkyl, aminoalkyl, alkylaminoalkyl, dialkylaminoalkyl or alkoxyalkyl), —COOR, -(alkenylene)-COOR, -(alkylene)-COOR (where R is hydrogen or alkyl), —CONR'R" and -(alkylene)-CONR'R" (where R' and R" are independently selected from hydrogen, alkyl, cycloalkyl or cycloalkylalkyl). More specifically the term heteroaryl includes, but is not limited to, pyridyl, pyrimidinyl, thiophen-2-yl, quinolyl, benzopyranyl, thiazolyl, imidazolyl and derivatives thereof.

"Optionally substituted heteroaryl" means a pyridyl, pyrimidinyl, thiophen-2-yl, quinolyl, benzopyranyl, thiazolyl or imidazolyl ring which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heteroalkyl" means an alkyl, alkenyl, alkynyl or cycloalkyl radical as defined above, carrying one or two substituents selected from —NR$^a$R$^b$, —OR$^c$, —S(O)$_n$R$^d$ or —SO$_3^-$X$^+$ wherein n is an integer from 0 to 2, X$^+$ is an alkali metal, R$^a$ is hydrogen, alkyl, haloalkyl, cycloalkyl, cycloalkylalkyl, hydroxy, amino, cyanoalkyl, hydroxyalkyl, alkoxyalkyl, aminoalkyl, alkylaminoalkyl, dialkylaminoalkyl, optionally substituted phenyl, optionally substituted heteroaryl, optionally substituted heterocyclylalkyl, optionally substituted heteroaralkyl —SO$_2$R (where R is alkyl), —SO$_2$NRR' (where R and R' are, independently of each other, hydrogen, alkyl, hydroxyalkyl, alkoxyalkyl, amninoalkyl, alkylaminoalkyl or dialkylaminoalkyl) or -(alkylene)-COOR (where R is hydrogen or alkyl), R$^b$ is hydrogen, alkyl, hydroxyalkyl, alkoxyalkyl, aminoalkyl, alkylaminoalkyl, dialkylaminoalkyl or optionally substituted heteroaralkyl, If is hydrogen, alkyl, haloalkyl, cycloalkyl, cycloalkylalkyl, hydroxyalkyl, alkoxyalkyl, arninoalkyl, alkylaminoalkyl, dialkylaminoalkyl, —COR (where R is alkyl, haloalkyl, cycloalkyl or cycloalkylalkyl) or -(alkylene)-COOR (where R is hydrogen or alkyl) and R$^d$ is hydrogen, alkyl, cycloalkyl, cycloalkylalkyl, hydroxyalkyl, alkoxyalkyl, aminoalkyl, alkylaminoalkyl, dialkylaminoalkyl or —NRR' (where R and R' are independently of each other hydrogen, alkyl, hydroxyalkyl, alkoxyalkyl, aminoalkyl, alkylaminoalkyl or dialkylaminoalkyl). Representative examples include, but are not limited to, 2-methoxyethyl, phenoxymethyl, 2-aminoethyl, 2-dimethylaminoethyl, 2-hydroxyethoxy, 2-dimethylaminoethoxy, and the like.

"Heterocycle" or "Heterocyclyl" means a cyclic radical of 3 to 8 ring atoms in which one: or two ring atoms are heteroatoms selected from N, O or S(O)$_n$ (where n is an integer from 0 to 2), the remaining ring atoms being C where one or two C atoms may optionally be replaced by a carbonyl group. The heterocycle ring may be optionally substituted independently with one or two substituents selected from alkyl, haloalkyl, cycloalkyl, cycloalkylalkyl, hydroxyalkyl, aminoalkyl, alkylaminoalkyl, dialkylaminoalkyl, alkoxyalkyl, optionally substituted phenyl, optionally substituted phenylalkyl, imidazole, halo, cyano, acyl, acylamino, —OR (where R is hydrogen, alkyl, haloalkyl, alkenyl, cycloalkyl, cycloalkylalkyl, optionally substituted phenyl, imidazole or optionally substituted phenylalkyl), —NRR' (where R and R' are independently selected from hydrogen, alkyl, cycloalkyl, cycloalkylalkyl, optionally substituted phenyl or optionally substituted phenylalkyl), —S(O)$_n$R (where n is an integer from 0 to 2 and R is hydrogen, alkyl, haloalkyl, alkenyl, cycloalkyl or cycloalkylalkyl), —SO$_2$NRR' (where R and R' are independently hydrogen, alkyl, alkenyl, heteroalkyl, haloalkyl, cycloalkyl, cycloalkylalkyl, optionally substituted phenyl or optionally substituted phenylalkyl), an amino protecting group, —COOR, -(alkylene)-COOR (where R is hydrogen or alkyl), —CONR'R" or -(alkylene)-CONR'R" (where R' and R" are independently selected from hydrogen, alkyl, cycloalkyl, cycloalkylalkyl, optionally substituted phenyl or optionally substituted phenylalkyl). More specifically the term heterocycle includes, but is not limited to, tetrahydropyranyl, pyrrolidine, piperidine, piperazine, homopiperazine, morpholine, thiomorpholine, azepine, and derivatives thereof.

"Optionally substituted heterocyclyl" means a tetrahydropyranyl, pyrrolidino, piperidino, piperazino, homopiperazino or morpholino ring which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Hydroxyalkyl" means an alkyl radical as defined above, carrying one or more, preferably one, two or three hydroxy groups, provided that if two hydroxy groups are present they are not both on the same carbon atom. Representative examples include, but are not limited to, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3hydroxypropyl, preferably 2-hydroxyethyl, 2,3-dihydroxypropyl, and 1-(hydroxymethyl)-2-hydroxyethyl.

"Aminoalkyl" means an alkyl radical as defined above, carrying one or two amino groups, e,g., 2-aminoethyl, 2-aminopropyl, 3-aminopropyl, 1-(aminomethyl)-2-methylpropyl, and the like.

"Alkylaminoalkyl" means an alkyl radical as defined above, carrying one or two —NHR groups where R is an alkyl group as defined above. Representative examples include, but are not limited to, 2-methylaminoethyl, 3-ethylaminopropyl, 1-(methylaminomethyl)-2-methylpropyl, and the like.

"Dialkylaminoalkyl" means an alkyl radical as defined above, carrying one or two —NRR groups where R is an alkyl group as defined above. Representative examples include, but are not limited to, 2-dimethylaminoethyl, 2-dimethylaminopropyl, 1-(dimethylamino-methyl)-2-methylpropyl, and the like.

"Alkoxyalkyl" means an alkyl radical as defined above, carrying one or two alkoxy group as defined above, e.g., 2-methoxyethyl, 2-methoxypropyl, and the like.

"Cycloalkylalkyl" means a radical —R$^a$R$^b$ where R$^a$ is an alkylene group and R$^b$ is a cycloalkyl group as defined above e.g., cyclopropylmethyl, cyclohexylpropyl, 3-cyclohexyl-2-methylpropyl, and the like.

"Aralkyl" means a radical —R$^a$R$^b$ where R$^a$ is an alkylene group and R$^b$ is an aryl group as defined above e.g., benzyl, phenylethyl, 3-(3-chlorophenyl)-2-methylpentyl, and the like.

"Heteroaralkyl" means a radical —R$^a$R$^b$ where R$^a$ is an alkylene group and R$^b$ is a heteroaryl group as defined above e.g., pyridin-3-ylmethyl, 3-(benzofuran-2-yl)propyl, and the like.

"Heterocyclylalkyl" means a radical —R$^a$R$^b$ where R$^a$ is an alkylene group and R$^b$ is a heterocyclyl group as defined above e.g., 2-(morpholin-4-yl)ethyl, 3-(piperidin-1-yl)-2-methylpropyl, and the like.

"Optional" or "optionally" means that the subsequently described event or circumstance may but need not occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the heterocyclo group is not substituted with the alkyl group.

"Amino protecting group" refers to those organic groups intended to protect nitrogen atoms against undesirable reactions during synthetic procedures e.g., benzyl, benzyloxycarbonyl (CBZ), tert-butoxycarbonyl (Boc), trifluoroacetyl, and the like.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzene-sulfonic acid, 2-napthalenesulfonic acid, 4-toluenesulfonic acid, camphorsulfonic acid, 4-methylbicyclo[2.2.2]-oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamnine, N-methylglucamine, and the like.

"Pro-drugs" means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula (I), and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

Nomenclature

The nomenclature used in this application is generally based on the IUPAC recommendations, for example:

(i) a compound of Formula (I) where B is carbon, Q is —NR$^4$—, —O— or —S—, and

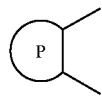

is a group of formula (S) is numbered and named as follows:

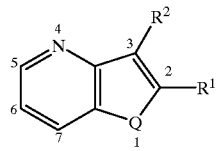

where Q is —NH—, R¹ is 4-pyridyl, R² is phenyl and R³ and R⁶ are hydrogen, is named as 3-phenyl-2-(pyridin-4-yl)-1H-pyrrolo[3,2-b]pyridine.

(ii) a compound of Formula (I) where B is carbon, Q is —NR⁴—, —O— or —S—, and

is a group of formula (T) is numbered and named as follows:

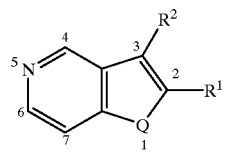

where Q is —NH, R¹ is 4-pyridyl, R² is phenyl and R³ and R⁶ are hydrogen, is named as 3 and -phenyl-2-(pyridin-4-yl)-1H-pyrrolo[3,2-c]pyridine.

(iii) a compound of Formula (I) where B is carbon, Q is —NR⁴—, —O— or —S—, and

is a group of formula (U) is named and numbered as follows:

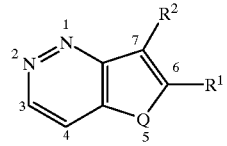

where Q is —NH—, R¹ is 4-pyridyl, R² is phenyl and R³ is hydrogen, is named as 7-phenyl-6-(pyridin-4-yl)-5H-pyrrolo[3,2-c]pyridazine.

(iv) a compound of Formula (I) where B is carbon, Q is —NR⁴—, —O— or —S—, and

is a group of formula (V) is named and numbered as follows:

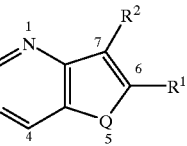

where Q is —NH—, R¹ is 4-pyridyl, R² is phenyl and R³ and R⁶ are hydrogen, is named as 7-phenyl-6-(pyridin-4-yl)-5H-pyrrolo[3,2-d]pyrimidine.

(v) a compound of Formula (I) where B is carbon, Q is —NR⁴—, —O— or —S—, and

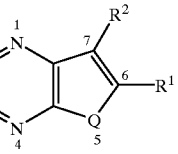

is a group of formula (W) is named and numbered as follows:

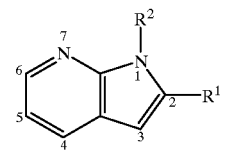

where Q is —NH—, R¹ is 4-pyridyl, R² is phenyl and R⁶ is hydrogen, is named as 7-phenyl-6-(pyridin-4-yl)-5H-pyrrolo[2,3-b]pyrazine.

(vi) a compound of Fonnula (I) where B is nitrogen, Q is —CH—, and

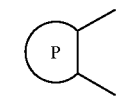

is a group of formula (S) is named and numbered as follows:

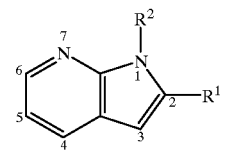

where R¹ is 4-pyridyl, R² is phenyl and R³ and R⁶ are hydrogen, is named as 1-phenyl-2-(pyridin-4-yl)-1H-pyrrolo[2,3-b]pyridine.

(vi) a compound of Formula (I) where B is nitrogen, Q is —CH—, and

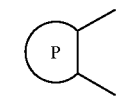

is a group of in formula (T) is named and numbered as follows:

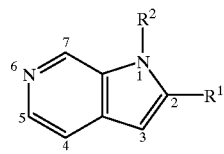

where $R^1$ is 4-pyridyl, $R^2$ is phenyl and $R^3$ and $R^6$ are hydrogen, is named as 1-phenyl-2-(pyridin-4-yl)-1H-pyrrolo[2,3-c]pyridine.

(vii) a compound of Formula (I) where B is nitrogen, Q is —CH—,

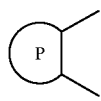

is a group of formula (U) is named and numbered as follows:

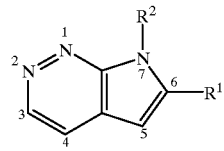

where $R^1$ is 4-pyridyl, $R^2$ is phenyl and $R^6$ is hydrogen, is named as 7-phenyl-6-(pyridin-4-yl)-7H-pyrrolo[2,3-c]pyridazine.

(viii) a compound of Formula (I) where B is nitrogen, Q is —CH—, and

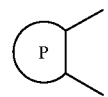

is a group of formula (V) is named and numbered as follows:

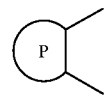

where Q is —NH—, $R^1$ is 4-pyridyl, $R^2$ is phenyl and $R^3$ and $R^6$ are hydrogen, is named as 7-phenyl-6-(pyridinyl)-7H-pyrrolo[2,3-d]pyrimidine.

Representative Compounds of this Invention are as Follows:

I. Compounds of Formula (I) where B is carbon, Q is —NR$^4$—, $R^3$ is hydrogen, is a group of formula (S), and the other groups are as defined below are:

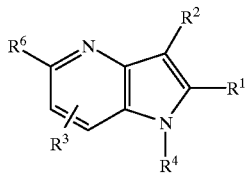

| CPD # | $R^1$ | $R^2$ | $R^4$ | $R^6$ | M.Pt. ° C. | Mass Spec. m/e |
|---|---|---|---|---|---|---|
| 1 | 4-pyridyl | 4-fluorophenyl | hydroxy | hydrogen | 225–228 | |
| 2 | 4-pyridyl | 4-fluorophenyl | methoxy | hydrogen | 168–171.5 | |
| 3 | 4-pyridyl | 4-fluorophenyl | 2-(morpholin-4-yl)ethoxy | hydrogen | 139–141 | |
| 4 | 4-pyridyl | 4-fluorophenyl | 2-(piperidin-1-yl)ethoxy | hydrogen | 95.9–98.7 | |
| 5 | 4-pyridyl | 4-fluorophenyl | 2-(pyrrolidin-1-yl)ethoxy | hydrogen | 123–129 | |
| 6 | 4-pyridyl | 4-fluorophenyl | hydrogen | hydrogen | >285 | |
| 7 | 4-pyridyl | 4-fluorophenyl | ethyl | hydrogen | 204–206 | |
| 8 | 4-pyridyl | 4-fluorophenyl | 2-(morpholin-4-yl)ethyl | hydrogen | 171.2–173 | |
| 9 | 4-pyridyl | 4-fluorophenyl | 2-(piperidin-1-yl)ethyl | hydrogen | 148.1–153.3 | |
| 10 | 4-pyridyl | 4-fluorophenyl | 3-dimethylaminopropyl | hydrogen | | 375 |
| 11 | 4-pyridyl | 4-fluorophenyl | 2-(1-methylpyrrolidin-2-yl)ethyl | hydrogen | | 401 |
| 12 | 4-pyridyl | 4-fluorophenyl | 3-hydroxypropyl | hydrogen | | 348 |
| 13 | 4-pyridyl | 4-fluorophenyl | 3-(1-methylpiperazin-4-yl)propyl | hydrogen | | 430 |
| 14 | 4-pyridyl | 4-fluorophenyl | 3-(trimethylamino)propyl.HCl salt | hydrogen | | 390 |
| 15 | 4-pyridyl | 4-fluorophenyl | 2-(RS)-(dimethylaminomethyl)propyl | hydrogen | | 389 |
| 16 | 4-pyridyl | 4-fluorophenyl | 3-cyanopropyl | hydrogen | | 357 |
| 17 | 4-pyridyl | 4-fluorophenyl | 2-aminocarbonylethyl | hydrogen | | 361 |
| 18 | 4-pyridyl | 4-fluorophenyl | ethyl.dihydrochloride | hydrogen | >285 | |
| 19 | 4-pyridyl | 4-fluorophenyl | dimethylaminocarbonylmethyl.TFA salt. | hydrogen | | 375 |
| 20 | 4-pyridyl | 4-fluorophenyl | methylmethoxyaminocarbonylmethyl.TFA salt. | hydrogen | | 391 |
| 21 | 4-pyridyl | 4-fluorophenyl | —CH$_2$COCH$_2$CO$_2$CH$_3$.TFA salt. | hydrogen | | 404 |
| 22 | 4-pyridyl | 4-fluorophenyl | —CH$_2$COCH$_3$.TFA salt. | hydrogen | | 346 |

-continued

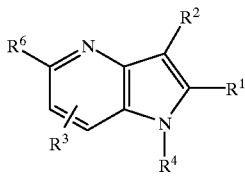

| CPD # | R¹ | R² | R⁴ | R⁶ | M.Pt. ° C. | Mass Spec. m/e |
|---|---|---|---|---|---|---|
| 23 | 4-pyridyl | 4-fluorophenyl | —(CH₂)₃NH(CH₂)₂NH₂.3 TFA salt. | hydrogen | | 390 |
| 24 | 4-pyridyl | 4-fluorophenyl | 3-(3-aminocarbonylpiperidin-1-yl)propyl | hydrogen | | 458 |
| 25 | 4-pyridyl | 4-fluorophenyl | 3-(pipendin-1-yl)propyl | hydrogen | | 415 |
| 26 | 4-pyridyl | 4-fluorophenyl | 3-(piperazin-1-yl)propyl.3 TFA salt. | hydrogen | | 416 |
| 27 | 4-pyridyl | 4-fluorophenyl | 3-(homopiperazin-1-yl)propyl.3 TFA salt. | hydrogen | | 430 |
| 28 | 4-pyridyl | 4-fluorophenyl | 3-hydroxylaminopropyl.2 TFA salt. | hydrogen | | 363 |
| 29 | 4-pyridyl | 4-fluorophenyl | 3-(morpholin-4-yl)propyl.2 TFA salt. | hydrogen | | 417 |
| 30 | 4-pyridyl | 4-fluorophenyl | 3-(4-hydroxypiperidin-1-yl)propyl.2 TFA salt. | hydrogen | | 431 |
| 31 | 4-pyridyl | 4-fluorophenyl | 3-imidazol-1-ylpropyl.3 TFA salt | hydrogen | | 398 |
| 32 | 4-pyridyl | 4-fluorophenyl | 3-aminopropyl.2 TFA salt | hydrogen | | 347 |
| 33 | 4-pyridyl | 4-fluorophenyl | 3-(2-aminocarbonylpyrrolidin-1-yl)propyl.2 TFA salt | hydrogen | | |
| 34 | 4-pyridyl | 4-fluorophenyl | 3-[3-(2-hydroxyethyl)piperidin-1-yl]-propyl. 2 TFA salt | hydrogen | | 459 |
| 35 | 4-pyridyl | 4-fluorophenyl | 3-[2-(hydroxymethyl)piperidin-1-yl]-propyl. 2 TFA salt | hydrogen | | 445 |
| 36 | 4-pyridyl | 4-fluorophenyl | 3-(pyrrolidin-1-yl)propyl.2 TFA salt | hydrogen | | 401 |
| 37 | 4-pyridyl | 4-fluorophenyl | 3-(3-hydroxypyrrolidin-1-yl)propyl. 2 TFA salt | hydrogen | | 431 |
| 38 | 4-pyridyl | 4-fluorophenyl | 3-{[tris(hydroxymethyl)methyl]amino}-propyl.2 TFA salt | hydrogen | | 451 |
| 39 | 4-pyridyl | 4-fluorophenyl | 3-[3-(hydroxymethyl)piperidin-1-yl)-propyl. | hydrogen | | 445 |
| 40 | 4-pyridyl | 4-fluorophenyl | 3-[(5-aminocarbonylimidazol-4-yl)-amino]propyl.2 TFA salt | hydrogen | | 456 |
| 41 | 4-pyridyl | 4-fluorophenyl | 3-[3-hydroxypropylamino]propyl.2 TFA salt | hydrogen | | 405 |
| 42 | 4-pyridyl | 4-fluorophenyl | 3-[(pipenzin-1-ylethyl)amino]propyl.2 TFA salt | hydrogen | | 459 |
| 43 | 4-pyridyl | 4-fluorophenyl | 2-methoxyethyl.2 HCl salt | hydrogen | 54–59 | |
| 44 | 4-pyridyl | 4-fluorophenyl | methyl.HCl salt | hydrogen | 219–220 | |
| 45 | 4-pyridyl | 4-fluorophenyl | 3-(3-aminopiperidin-1-yl)propyl.3 TFA salt | hydrogen | | 430 |
| 46 | 4-pyridyl | 4-fluorophenyl | 3-(3-hydroxypyrrolidin-1-yl)propyl.2 TFA salt | hydrogen | | 417 |
| 47 | 4-pyridyl | 4-fluorophenyl | 3-[(tetrahydropyran-2-ylmethyl)amino]propyl 2 TFA salt | hydrogen | | 431 |
| 48 | 4-pyridyl | 4-fluorophenyl | 3-(2,6-dimethylmorpholin-4-yl)propyl.2 TFA salt | hydrogen | | 445 |
| 49 | 4-pyridyl | 4-fluorophenyl | aminocarbonylmethyl.TFA salt | hydrogen | | 347 |
| 50 | 4-pyridyl | 4-fluorophenyl | —(CH₂)₂SO₃⁻ Na⁺ salt | hydrogen | | 398 |
| 51 | 4-pyridyl | 4-fluorophenyl | —(CH₂)₂CH(SO₃⁻)(CH₂)₃SO₃⁻.2 Na⁺ salt | hydrogen | | 534 |
| 52 | 4-pyridyl | 4-fluorophenyl | carboxymethyl.TFA salt | hydrogen | | 348 |
| 53 | 4-pyridyl | 4-fluorophenyl | 4-(morpholin-4-yl)butyl.2 TFA salt | hydrogen | | 431 |
| 54 | 4-pyridyl | 4-fluorophenyl | 4-methylaminobutyl.2 TFA salt | hydrogen | | |
| 55 | 4-pyridyl | 4-fluorophenyl | 4-(pyrrolidin-1-yl)butyl.2 TFA salt | hydrogen | | 415 |
| 56 | 4-pyridyl | 4-fluorophenyl | 4-(piperidin-1-yl)butyl.2 TFA salt | hydrogen | | 429 |
| 57 | 4-pyridyl | 4-fluorophenyl | 2-hydroxyethyl.2 HCl salt | hydrogen | 232.8–237.9 | |
| 58 | 4-pyridyl | 4-fluorophenyl | —(CH₂)₃SO₃⁻ Na⁺ salt.TFA salt | hydrogen | | 412 |
| 59 | 4-pyridyl | 4-fluorophenyl | carboxymethylaminocarbonylmethyl.HCl | hydrogen | | 405 |
| 60 | 4-pyridyl | 4-fluorophenyl | cyanomethyl | hydrogen | 233.1–233.7 | |
| 61 | 4-pyridyl | 4-fluorophenyl | 2-(pyrrolidin-1-yl)ethyl | hydrogen | 148.1–153.3 | |
| 62 | 4-pyridyl | 4-fluorophenyl | 3-[bis(2-hydroxyethyl)amino]propyl.2 TFA salt | hydrogen | | 435 |
| 63 | 4-pyridyl | 4-fluorophenyl | 3-(cyanomethylamino)propyl.2 TFA salt | hydrogen | | 386 |
| 64 | 4-pyridyl | 4-fluorophenyl | 2-aminoethyl.2 TFA salt | hydrogen | | 333 |
| 65 | 4-pyridyl | 4-fluorophenyl | 4-aminobutyl.2 TFA salt | hydrogen | | 361 |
| 66 | 4-pyridyl | 4-fluorophenyl | 2-(4-methylpiperazin-1-yl)ethyl.3 TFA salt | hydrogen | | 416 |
| 67 | 4-pyridyl | 4-fluorophenyl | 2-imidazol-1-ylethyl.2 TFA salt | hydrogen | | 384 |
| 68 | 4-pyridyl | 4-fluorophenyl | 2-cyanoethyl | hydrogen | 171.3–172.5 | |
| 69 | 4-pyridyl | 4-fluorophenyl | methylsulfonyl | hydrogen | 206.6–207.1 | |
| 70 | 4-pyridyl | 4-fluorophenyl | 1-(hydroxymethyl)propyl | hydrogen | 176.6–178.2 | |
| 71 | 4-pyridyl | 4-fluorophenyl | 4-cyanobutyl.TFA | hydrogen | | 371 |
| 72 | 4-pyridyl | 4-fluorophenyl | 3-guanidinopropyl.2 TFA | hydrogen | | 389 |
| 73 | 4-pyridyl | 4-fluorophenyl | 2-guanidinoethyl.2 TFA | hydrogen | | 375 |
| 74 | 4-pyridyl | 4-fluorophenyl | 3-(4-methylimidazol-1-yl)propyl.2 TFA | hydrogen | | |
| 75 | 4-pyridyl | 4-fluorophenyl | 3-(2-nitroimidazol-1-yl)propyl.2 HCl | hydrogen | | |
| 76 | 4-pyridyl | 4-fluorophenyl | 3-(2-methylimidazol-1-yl)propyl.2 TFA | hydrogen | | |

-continued

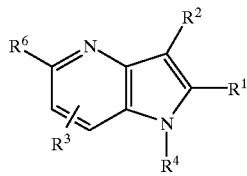

| CPD # | R¹ | R² | R⁴ | R⁶ | M.Pt. ° C. | Mass Spec. m/e |
|---|---|---|---|---|---|---|
| 77 | 4-pyridyl | 4-fluorophenyl | hydrogen | methoxy | 244 | |
| 78 | 4-pyridyl | 4-fluorophenyl | 3-[N,N-bis(pyridin-3-ylmethyl)amino]propyl | hydrogen | | |
| 79 | 4-pyridyl | 4-fluorophenyl | —(CH₂)₃N[(CH₂)₃N(CH₃)₂]₂ | hydrogen | | |

II. Compounds of Formula (I) where B is carbon, Q is —NR⁴—,

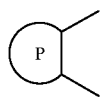   20 is a group of formula (S), and the other groups are as defined below are:

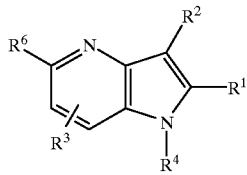

| CPD # | R¹ | R³ | R² | R⁴ | R⁶ | M.Pt. ° C. | Mass Spec. |
|---|---|---|---|---|---|---|---|
| 80 | 4-pyridyl | hydrogen | 3-chloro-4-fluoro-phenyl | hydrogen | hydrogen | 293.5–296.5 | |
| 81 | 4-pyridyl | hydrogen | 3-chlorophenyl | hydrogen | hydrogen | >280 | |
| 82 | 4-pyridyl | hydrogen | 3-trifluoromethyl phenyl | hydrogen | hydrogen | 226.2–226.9 | |
| 83 | 4-pyridyl | hydrogen | 3-methoxyphenyl | hydrogen | hydrogen | 240.4–240.6 | |
| 84 | 4-pyridyl | hydrogen | 2-methylphenyl | hydrogen | hydrogen | >300 | |
| 85 | 4-pyridyl | hydrogen | 2-methoxyphenyl | hydrogen | hydrogen | >300 | |
| 86 | 4-pyridyl | hydrogen | 3-trifluoromethyl-phenyl | methyl | hydrogen.HCl | 220–252 | |
| 87 | 4-pyridyl | hydrogen | 3-chloro-4-fluoro-phenyl | methyl | hydrogen.HCl | 220–230 | |
| 88 | 4-pyridyl | hydrogen | 4-fluorophenyl | methyl | chloro.HCl | 250–252 | |
| 89 | 4-pyridyl | hydrogen | 4-fluorophenyl | hydrogen | ethyl.2HCl | 195–199 | |
| 90 | 4-pyridyl | hydrogen | 4-fluorophenyl | hydrogen | methoxy.2 HCl | 244 | |
| 91 | 4-pyridyl | 6-chloro | 4-fluorophenyl | hydrogen | hydrogen | 229.5–231.2 | |
| 92 | 4-pyridyl | 6-trifluoro-methyl | 4-fluorophenyl | 2-morpholin-4-ylethoxy | hydrogen | 126.4–128.2 | |
| 93 | 2-(2-hydroxyethyl-amino)-4-pyridyl | hydrogen | 4-fluorophenyl | hydrogen | hydrogen.HCl | | 349 |
| 94 | 2-[HO(CH₂)₂O(CH₂)₂—NH]-4-pyridyl | hydrogen | 4-fluorophenyl | hydrogen | hydrogen.HCl | | 393 |
| 95 | 2-(2-methylamino-ethylamino)-4-pyridyl | hydrogen | 4-fluorophenyl | hydrogen | hydrogen.HCl | | 379 |
| 96 | 2-(3-methoxypropyl-amino)-4-pyridyl | hydrogen | 4-fluorophenyl | hydrogen | hydrogen.HCl | | 393 |
| 97 | 2-n-propylamino-4-pyridyl | hydrogen | 4-fluorophenyl | hydrogen | hydrogen.HCl | | 361 |
| 98 | 2-(3-hydroxypropyl-amino)-4-pyridyl | hydrogen | 4-fluorophenyl | hydrogen | hydrogen.HCl | | 363 |
| 99 | 2-methylamino-4-pyridyl | hydrogen | 4-fluorophenyl | hydrogen | hydrogen.HCl | | 320 |

-continued

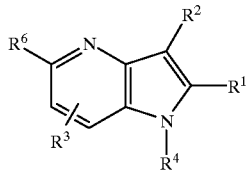

| CPD # | R¹ | R³ | R² | R⁴ | R⁶ | M.Pt. °C. | Mass Spec. |
|---|---|---|---|---|---|---|---|
| 100 | 2-acetylamino-4-pyridyl | hydrogen | 4-fluorophenyl | hydrogen.HCl | hydrogen | | 347 |

III. Compounds of Formula (I) where B is carbon, Q is —O—, $R^3$ and $R^6$ are hydrogen,

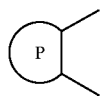

is a group of formula (S), and the other groups are as defined below are:

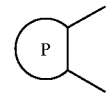

| CPD # | R¹ | R² | M.Pt. °C. |
|---|---|---|---|
| 101 | 4-pyridyl | 4-fluorophenyl | 141–143 |
| 102 | 2-chloropyrimidin-4-yl | 4-fluorophenyl | 224.8–225.2 |
| 103 | 2-aminopyrimidin-4-yl | 4-fluorophenyl | 252.9–253.7 |
| 104 | 2-methylthiopyrimidin-4-yl | 4-fluorophenyl | 182.5–183.9 |

IV. Compounds of Formula (I) where B is carbon, Q is —$NR^4$—, $R^3$ and $R^6$ are hydrogen, is a group of formula (T), and the other groups are as defined below is:

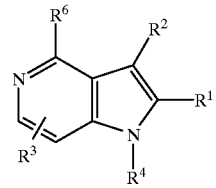

| CPD # | R¹ | R² | R⁴ | M.Pt. °C. |
|---|---|---|---|---|
| 105 | 4-pyridyl | 4-fluorophenyl | hydrogen | 256–257 |

V. Compounds of Formula (I) where B is carbon, Q is —$NR^4$—, $R^6$ is hydrogen,

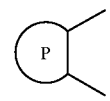

is a group of formula (W), and the other groups are as defined below is:

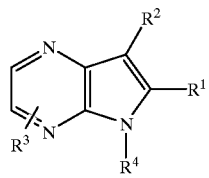

| CPD # | R¹ | R² | R⁴ | Mass Spec. m/e |
|---|---|---|---|---|
| 106 | 4-pyridyl | 4-fluorophenyl | hydrogen | |
| 107 | 4-pyridyl | 4-fluorophenyl | hydrogen.HCl salt | |
| 108 | 4-pyridyl | 4-fluorophenyl | 3-cyanopropyl | 358 |

-continued

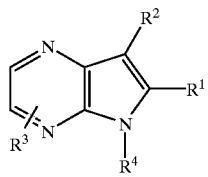

| CPD # | R¹ | R² | R⁴ | Mass Spec. m/e |
|---|---|---|---|---|
| 109 | 4-pyridyl | 4-fluorophenyl | 3-(imidazol-1-yl)propyl | 399 |
| 110 | 4-pyridyl | 4-fluorophenyl | methyl.HCl salt | 305 |
| 111 | 4-pyridyl | 4-fluorophenyl | ethyl.HCl salt | 318 |
| 112 | 2-[(2-hydroxyethyl)amino]-4-pyridyl | 4-fluorophenyl | hydrogen.HCl salt | 350 |
| 113 | 2-[(2-aminoethyl)amino]-4-pyridyl | 4-fluorophenyl | hydrogen.HCl salt | 349 |
| 114 | 2-[(3-hydroxypropyl)amino]-4-pyridyl | 4-fluorophenyl | hydrogen.HCl salt | 364 |
| 115 | 2-methylamino-4-pyridyl | 4-fluorophenyl | hydrogen.HCl salt | 320 |
| 116 | 2-bromo-4-pyridyl | 4-fluorophenyl | hydrogen.HCl salt | 369 |
| 117 | 2-methoxy-4-pyridyl | 4-fluorophenyl | hydrogen.HCl salt | 321 |
| 118 | 2-[(3-aminopropyl)amino]-4-pyridyl | 4-fluorophenyl | hydrogen.HCl salt | 363 |
| 119 | 2-hydroxylamino-4-pyridyl | 4-fluorophenyl | hydrogen.HCl salt | 322 |
| 120 | 2-carboxymethylamino-4-pyridyl | 4-fluorophenyl | hydrogen.HCl salt | 364 |
| 121 | 4-pyridyl | 4-fluorophenyl | 3-(2-nitroimidazol-1-yl)propyl.HCl salt | 444 |
| 122 | 4-pyridyl | 4-fluorophenyl | 3-(4-methylimidazol-1-yl)propyl.HCl salt | 413 |
| 123 | 4-pyridyl | 4-fluorophenyl | 3-(4-methylpiperazin-1-yl)propyl.HCl salt | 431 |
| 124 | 4-pyridyl | 4-fluorophenyl | 3-(morpholin-4-yl)propyl.HCl salt | 418 |
| 125 | 4-pyridyl | 4-fluorophenyl | 3-methylaminopropyl.HCl salt | 362 |
| 126 | 4-pyridyl | 4-fluorophenyl | 3-(4-nitroimidazol-1-yl)propyl.HCl salt | 444 |
| 127 | 2-acetylamino-4-pyridyl | 4-fluorophenyl | hydrogen.HCl | 348 |

VI. Compounds of Formula (I) where B is carbon, Q is —NR⁴—, R⁶ is hydrogen,

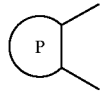

is a group of formula (W), and the other groups are as defined below is:

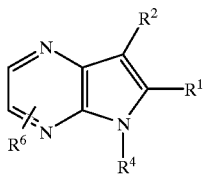

| CPD # | R¹ | R² | R⁶ | R⁴ | Mass Spec. m/e |
|---|---|---|---|---|---|
| 128 | 2-methylamino-4-pyridyl | 4-fluorophenyl | 6-methylamino | hydrogen.2 HCl | 349 |
| 129 | 2-imidazol-1-ylmethyl-carbonylamino-4-pyridyl | 4-fluorophenyl | hydrogen | hydrogen.2 HCl | 414 |
| 130 | 2-dimethylaminomethyl-carbonylamino-4-pyridyl | 4-fluorophenyl | hydrogen | hydrogen.2 HCl | 391 |
| 131 | 2-methylaminomethyl-carbonylamino-4-pyridyl | 4-fluorophenyl | hydrogen | hydrogen.2 HCl | 377 |
| 132 | 2-piperidin-1-ylmethyl-carbonylamino-4-pyridyl | 4-fluorophenyl | hydrogen | hydrogen.2 HCl | 431 |
| 133 | 2-(4-methylpiperazin-1-yl-methylcarbonylamino-4-pyridyl | 4-fluorophenyl | hydrogen | hydrogen.2 HCl | 446 |
| 134 | 4-pyridyl | 4-fluorophenyl | 6-dimethylamino | hydrogen.2 HCl | 334 |

-continued

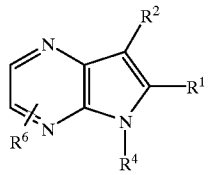

| CPD # | R¹ | R² | R⁶ | R⁴ | Mass Spec. m/e |
|---|---|---|---|---|---|
| 135 | 4-pyridyl | 4-fluorophenyl | 6-methoxy | hydrogen.HCl | 321 |
| 136 | 4-pyridyl | 4-fluorophenyl | 6-methylthio | hydrogen.HCl | 337 |
| 137 | 2-(2-methylthioethylamino)-4-pyridyl | 3-chlorophenyl | hydrogen | hydrogen.2 HCl | 396 |
| 138 | 4-pyridyl | 4-fluorophenyl | 6-acetylamino | hydrogen.HCl | 348 |
| 139 | 2-(2-hydroxyethylamino)-4-pyridyl | 4-fluorophenyl | 6-methylamino | hydrogen.2 HCl | 379 |
| 140 | 2-acetylamino-4-pyridyl | 4-fluorophenyl | 6-acetylamino | hydrogen.HCl | 405 |
| 141 | 2-methoxymethylcarbonyl-amino-4-pyridyl | 4-fluorophenyl | hydrogen | hydrogen HCl | 378 |
| 142 | 2-(2-dimethylaminoethyl-carbonylamino)-4-pyridyl | 4-fluorophenyl | hydrogen | hydrogen.2 HCl | 405 |
| 143 | 2-chloro-4-pyridyl | 3-chlorophenyl | hydrogen | hydrogen.HCl | 341 |
| 144 | 2-chloro-4-pyridyl | 4-fluorophenyl | 6-chloro | hydrogen.HCl | 359 |
| 145 | 2-(2-hydroxyethylamino)-4-pyridyl | 4-fluorophenyl | 6-(2-hydroxyethyl-amino) | hydrogen.2 HCl | 409 |
| 146 | 2-(3-hydroxypropylamino)-4-pyridyl | 4-fluorophenyl | 6-(3-hydroxypropyl-amino) | hydrogen.2 HCl | 437 |
| 147 | 2-(4-hydroxybutylamino)-4-pyridyl | 4-fluorophenyl | 6-(4-hydroxybutyl-amino) | hydrogen.2 HCl | 466 |
| 148 | 2-(2-methoxyethylamino)-4-pyridyl | 4-fluorophenyl | 6-(2-methoxyethyl-amino) | hydrogen.2 HCl | 437 |
| 149 | 2-(3-methoxypropylamino)-4-pyridyl | 4-fluorophenyl | 6-(3-methoxypropyl-amino) | hydrogen.2 HCl | 465 |
| 150 | 2-(3-aminopropylamino)-4-pyridyl | 4-fluorophenyl | 6-(3-aminopropyl-amino) | hydrogen.4 HCl | 435 |

VII. Compounds of Formula (I) where B is nitrogen, Q is —CH—, R⁶ is hydrogen,

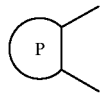

is a group of formula (S), and the other groups are as defined below are:

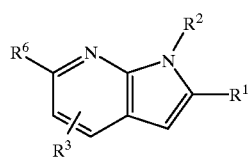

| CPD # | R¹ | R² | R³ | M.Pt. ° C. |
|---|---|---|---|---|
| 151 | 4-fluorophenyl | 4-pyridyl | 5-methyl | 202.1–206 |

VIII. Compounds of Formula (I) where B is carbon, Q is —NH—, R³ and R⁶ are hydrogen,

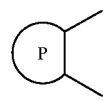

is a group of formula (V), and the other groups are as defined below are:

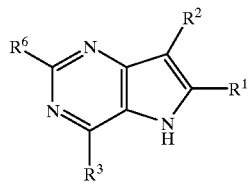

| CPD # | R¹ | R² | Mass Spec. m/e |
|---|---|---|---|
| 152 | 4-pyridyl | 4-fluorophenyl | 290 |

PREFERRED EMBODIMENTS

While the broadest definition of this invention is set forth in the Summary of the Invention, certain compounds of Formula (I) are preferred. For example, A preferred group of compounds is that wherein - - - - - - is between B and —CR¹—.

Within this group, more preferred groups are as follows:

I. One more preferred group of compounds is that wherein:
Q is —NR⁴—; and

is a group represented by formula (S).

Within these preferred and more preferred groups, an even more preferred group of compounds is that wherein:

(A)
- $R^2$ is aryl;
- $R^3$ is at the 7-position and is hydrogen, alkyl, halo or heteroalkyl, more preferably hydrogen, methyl, chloro, fluoro, 2-hydroxyethyl, 2-aminoethyl or 2-dimethylaminoethyl, most preferably hydrogen; and
- $R^6$ is hydrogen, alkyl, alkoxy or halo, preferably hydrogen, methyl, methoxy, fluoro or chloro, most preferably hydrogen.

Within these preferred, more preferred and even more preferred groups, a particularly preferred group of compounds is that wherein:
- $R^1$ is a 4-pyridyl or 4-pyrimidinyl ring optionally substituted with a substituent selected from heteroalkyl, —NRR' (where R and R' are independently of each other hydrogen, alkyl, heterocyclylalkyl or heteroalkyl), —NR$^a$C(O)R$^b$ [where R$^a$ is hydrogen or alkyl and R$_b$ is hydrogen, alkyl or -(alkylene)-X where X is hydroxy, alkoxy, amino, alkylamino, dialkylanino, cycloalkyl, heterocyclyl, optionally substituted phenyl, imidazole or —S(O)$_n$R' (where n is 0 to 2 and R' is alkyl)], —NRSO$_2$R" [where R is hydrogen or alkyl and R" is alkyl or -(alkylene)-X where X is hydroxy, alkoxy, amino, alkylamino, dialkylamino or —S(O)$_n$R' (where n is 0 to 2 and R' is alkyl)] or —OR (where R is alkyl or heteroalkyl), more preferably $R^1$ is a 4-pyridyl ring optionally substituted at the 2-position with a substituent selected from amino, acetylamino, methylamino, dimethylamino, methylsulfonylamino, 2-hydroxyethyl, 2-hydroxyethylamino, 3-hydroxypropyamino, 2-aminoethylamino, 2-aminoethyl, 3-aminopropyl, 2-dimethylaminoethyl, methoxy, 2-hydroxyethoxy or 2-dimethylaminoethoxy, most preferably 2-acetylamino-4-pyridyl or 2-(2-hydroxyethylamino)-4-pyridyl; and
- $R^2$ is a phenyl ring optionally substituted with one or two substituents selected from alkyl, halo or —OR (where R is alkyl), more preferably a phenyl ring substituted with one or two substituents selected from methyl, fluoro, chloro or methoxy, most preferably 4-fluorophenyl.

Within these preferred, more preferred and particularly preferred groups, an even more preferred group of compounds is that wherein:
- $R^4$ is hydrogen, alkyl, heteroalkyl, heterocyclylalkyl, -(alkylene)-Z or -(alkylene)-CO-(alkylene)-Z wherein:
  Z is —COOR$^7$ where R$^7$ is alkyl;
  —CONR$^8$R$^9$ where R$^8$ is hydrogen or alkyl, R$^9$ is alkoxy or -(alkylene)-COOR$^7$, or R$^8$ and R$^9$ together with the nitrogen atom to which they are attached form a heterocycle; or
  —C(=NR$^{10}$)(NR$^{11}$R$^{12}$) where R$^{10}$, R$^{11}$ and R$^{12}$ independently represent hydrogen or alkyl, or R$^{10}$ and R$^{11}$ together are —(CH$_2$)$_n$— where n is 2 or 3 and $R^{12}$ is hydrogen or alkyl; preferably hydrogen, methyl, ethyl, 2-hydroxyethyl, 3-hydroxypropyl, 2-aminoethyl, 3-aminopropyl, 2-methylaminoethyl, 3-methylaminopropyl, 2-dimethylaminoethyl, 3-dimethylaminopropyl, 2-(morpholin-4-yl)ethyl, 3-(morpholin-4-yl)propyl, 2-(piperidin-1-yl)ethyl, 3-(piperidin-1-yl)propyl, 2-(piperazin-1-yl)ethyl, 3-(piperazin-1-yl)propyl, more preferably hydrogen, methyl, 2-(morpholin-4-yl)ethyl, or 2-(piperidin-1-yl)ethyl.

(B) Another even more preferred group of compounds is that wherein:
- $R^1$ is a heteroaryl ring substituted with —NRR' (where R is hydrogen, alkyl, heterocyclylalkyl or heteroalkyl and R' is heterocyclylalkyl or heteroalkyl), preferably a 4-pyridyl or 4-pyrimidinyl ring substituted at the 2-position with —NRR' (where R is hydrogen, alkyl, heterocyclylalkyl or heteroalkyl and R is heterocyclylalkyl or heteroalkyl), more preferably 2-hydroxyethylaminopyridyl, 2-dimethylaminoethylamino-4-pyridyl, or 2-methylaminoethylamino-4-pyridyl; and
- $R^2$ is aryl.

Within these preferred, more preferred and even more preferred groups, a particularly preferred group of compounds is that wherein:
- $R^2$ is a phenyl ring optionally substituted with one or two substituents selected from alkyl, halo or —OR (where R is alkyl), more preferably a phenyl ring substituted with one or two substituents selected from methyl, fluoro, chloro or methoxy, most preferably 4-fluorophenyl;
- $R^3$ is at the 7-position and is hydrogen, alkyl, halo or heteroalkyl, more preferably hydrogen, methyl, chloro, fluoro, 2-hydroxyethyl, 2-aminoethyl or 2-dimethylaminoethyl, most preferably hydrogen; and
- $R^6$ is hydrogen, alkyl, alkoxy or halo, preferably hydrogen, methyl, methoxy, fluoro or chloro, most preferably hydrogen.

Within these preferred, more preferred and particularly preferred groups, an even more preferred group of compounds is that wherein:
- $R^4$ is hydrogen, alkyl, heteroalkyl, heterocyclylalkyl, -(alkylene)-Z or -(alkylene)-CO-(alkylene)-Z wherein:
  Z is —COOR$^7$ where R$^7$ is alkyl;
  —CONR$^8$R$^9$ where R$^8$ is hydrogen or alkyl, R$^9$ is alkoxy or -(alkylene)-COOR$^7$, or R$^8$ and R$^9$ together with the nitrogen atom to which they are attached form a heterocycle; or
  —C(=NR$^{10}$)(NR$^{11}$R$^{12}$) where R$^{10}$, R$^{11}$ and R$^{12}$ independently represent hydrogen or alkyl, or R$^{10}$ and R$^{11}$ together are —(CH$_2$)$_n$— where n is 2 or 3; preferably hydrogen, methyl, ethyl, 2-hydroxyethyl, 3-hydroxypropyl, 2-aminoethyl, 3-aminopropyl, 2-methylaminoethyl, 3-methylaminopropyl, 2-dimethylaminoethyl, 3-dimethylaminopropyl, 2-(morpholin-4-yl)ethyl, 3-(morpholin-4-yl)propyl, 2-(piperidin-1-yl)ethyl, 3-(piperidin-1-yl)propyl, 2-(piperazin-1-yl)ethyl, 3-(piperazin-1-yl)propyl, more preferably hydrogen, methyl, 2-(morpholin-4-yl)ethyl, or 2-(piperidin-1-yl)ethyl.

II. A second more preferred group of compounds is that wherein:

Q is —NR⁴—; and

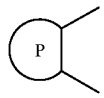

is a group represented by formula (W).

Within these preferred and more preferred groups, an even more preferred group of compounds is that wherein:
(A)
R⁶ is at the 6-position and is selected from hydrogen, alkyl, alkoxy, halo, —NRC(O)R" [where R is hydrogen, alkyl or hydroxyalkyl and R" is hydrogen, alkyl, cycloalkyl or -(alkylene)-X where X is hydroxy, alkoxy, amino, alkylamino, dialkylamino, heterocyclyl or —S(O)$_n$R' (where n is 0 to 2 and R' is alkyl)] or —NRSO₂R" [where R is hydrogen or alkyl and R" is alkyl or -(alkylene)-X where X is hydroxy, alkoxy, amino, alkylamino, dialkylamino or —S(O)$_n$R' (where n is 0 to 2 and R' is alkyl)], preferably hydrogen, methyl, methoxy, fluoro, chloro, amino, 2-hydroxyethylamino, or acetylamino, most preferably hydrogen.

Within these preferred and more preferred groups, particularly preferred group of compounds is that wherein:
R¹ is a 4-pyridyl or 4-pyrimidinyl ring optionally substituted with a substituent selected from heteroalkyl, —NRR' (where R and R' are, independently of each other, hydrogen, alkyl, heterocyclylalkyl or heteroalkyl), —NR$^a$C(O)R$^b$ [where R$^a$ is hydrogen or alkyl and R$^b$ is hydrogen, alkyl or -(alkylene)-X where X is hydroxy, alkoxy, amino, alkylamino, dialkylamino, cycloalkyl, heterocyclyl, optionally substituted phenyl, imidazole or —S(O)$_n$R' (where n is 0 to 2 and R' is alkyl)], —NRSO₂R" [where R is hydrogen or alkyl and R" is alkyl or -(alkylene)-X where X is hydroxy, alkoxy, amino, alkylamino, dialkylamino or —S(O)$_n$R' (where n is 0 to 2 and R' is alkyl)] or —OR (where R is alkyl or heteroalkyl), more preferably R¹ is a 4-pyridyl ring optionally substituted at the 2-position with a substituent selected from amino, acetylamino, methylamino, dimethylamino, methylsulfonylamino, 2-hydroxyethyl, 2-hydroxyethylamino, 3-hydroxypropylanino, 2-aminoethylamino, 2-aminoethyl, 3-aminopropyl, 2-dimethylaminoethyl, methoxy, 2-hydroxyethoxy or 2-dimethylaminoethoxy; and R² is an aryl ring, preferably a phenyl ring optionally substituted with one or two substituents selected from alkyl, halo or —OR (where R is alkyl), more preferably a phenyl ring substituted with one or two substituents selected from methyl, fluoro, chloro or methoxy, most preferably 4-fluorophenyl.

Within these preferred, more preferred and particularly preferred groups, an even more preferred group of compounds is that wherein:
R⁴ is hydrogen, alkyl, cycloalkyl, heteroalkyl, acyl, heterocyclylalkyl, -(alkylene)-Z or -(alkylene)-CO-(alkylene)-Z wherein:
Z is —COOR⁷ where R⁷ is alkyl;
—CONR⁸R⁹ where R⁸ is hydrogen or alkyl, R⁹ is alkoxy or -(alkylene)-COOR⁷, or R⁸ and R⁹ together with the nitrogen atom to which they are attached form a heterocycle; or
—C(=NR¹⁰)(NR¹¹R¹²) where R¹⁰, R¹¹ and R¹² independently represent hydrogen or alkyl, or R¹⁰ and R¹¹ together are —(CH₂)$_n$— where n is 2 or 3; preferably hydrogen, methyl, ethyl, 2-hydroxyethyl, 3-hydroxypropyl, 2-aminoethyl, 3-aminopropyl, 2-methylaminoethyl, 3-methylaminopropyl, 2-dimethylaminoethyl, 3-dimethylaminopropyl, 2-(morpholin-4-yl)ethyl, 3-(morpholin-4-yl)propyl, 2-(piperidin-1-yl)ethyl, 3-(piperidin-1-yl)propyl, 2-(piperazin-1-yl)ethyl, 3-(piperazin-1-yl)propyl, more preferably hydrogen, methyl, 2-(morpholin-4-yl)ethyl, or 2-(piperidin-1-yl)ethyl.

Another even more preferred group of compounds is that wherein:
(B)
R¹ is a heteroaryl ring substituted with —NRR' (where R is hydrogen, alkyl, heterocyclylalkyl or heteroalkyl and R' is heterocyclylalkyl or heteroalkyl), preferably a 4-pyridyl or 4-pyrimidinyl ring substituted at the 2-position with —NRR' (where R is hydrogen, alkyl, heterocyclylalkyl or heteroalkyl and R' is heterocyclylalkyl or heteroalkyl), preferably 2-hydroxyethylamino-4-pyridyl, 2-dimethylaminoethylamino-4-pyridyl, or 2-methylaminoethylamino-4-pyridyl; and R² is aryl.

Within these preferred, more preferred and even more preferred groups, a particularly preferred group of compounds is that wherein:
R⁴ is hydrogen, alkyl, cycloalkyl, heteroalkyl, acyl, heterocyclylalkyl, -(alkylene)-Z or -(alkylene)-CO-(alkylene)-Z wherein:
Z is —COOR⁷ where R⁷ is alkyl;
—CONR⁸R⁹ where R⁸ is hydrogen or alkyl, R⁹ is alkoxy or -(alkylene)-COOR⁷, or R⁸ and R⁹ together with the nitrogen atom to which they are attached form a heterocycle; or
—C(=NR¹⁰)(NR¹¹R¹²) where R¹⁰, R¹¹ and R¹² independently represent hydrogen or alkyl, or R¹⁰ and R¹¹ together are —(CH₂)$_n$— where n is 2 or 3; preferably hydrogen, methyl, ethyl, 2-hydroxyethyl, 3-hydroxypropyl, 2-aminoethyl, 3-aminopropyl, 2-methylaminoethyl, 3-methylaminopropyl, 2-dimethylaminoethyl, 3-dimethylaminopropyl, 2-(morpholin-4-yl)ethyl, 3-(morpholin-4-yl)propyl, 2-(piperidin-1-yl)ethyl, 3-(piperidin-1-yl)propyl, 2-(piperazin-1-yl)ethyl, 3-(piperazin-1-yl)propyl, more preferably hydrogen, methyl, 2-(morpholin-4-yl)ethyl, or 2-(piperidin-1-yl)ethyl; and R⁶ is at the 6-position of ring (W) and is selected from hydrogen, alkyl, alkoxy, halo, —NRC(O)R" [where R is hydrogen, alkyl or hydroxyalkyl and R" is hydrogen, alkyl, cycloalkyl or -(alkylene)-X where X is hydroxy, alkoxy, amino, alkylanmino, dialkylamino, heterocyclyl or —S(O)$_n$R' (where n is 0 to 2 and R' is alkyl)] or —NRSO₂R" [where R is hydrogen or alkyl and R" is alkyl or -(alkylene)-X where X is hydroxy, alkoxy, amino, alkylamino, dialkylamino or —S(O)$_n$R' (where n is 0 to 2 and R' is alkyl)], preferably hydrogen, methyl, methoxy, fluoro, chloro, amino or acetylamino, most preferably hydrogen.

Within these preferred and more preferred groups and particularly preferred groups, an even more preferred group of compounds is that wherein:
R² is an aryl ring, preferably a phenyl ring optionally substituted with one or two substituents selected from alkyl, halo or —OR (where R is alkyl), more preferably a phenyl ring substituted with one or two substituents selected from methyl, fluoro, chloro or methoxy, most preferably 4-fluorophenyl.

III. A third more preferred group of compounds is that wherein:

Q is —O—; and

is a group represented by formula (S).

Within these preferred and more preferred group of compounds, an even more referred group of compounds is that wherein:

$R^3$ is at the 7-position and is hydrogen, alkyl, cycloalkyl, heteroalkyl, halo, heterocyclylalkyl, —$OR^{19}$ (where $R^{19}$ is hydrogen, alkyl, heteroalkyl or heterocyclylalkyl), -(alkylene)-Z" or -(alkylene)-CO-(alkylene)-Z" wherein:

Z" is cyano;
—$COOR^{24}$ where $R^{24}$ is hydrogen or alkyl;
—$CONR^{25}R^{26}$ where $R^{25}$ and $R^{26}$ independently represent hydrogen or alkyl or and $R^{26}$ together with the nitrogen atom to which they are attached form a heterocycle;
—$C(=NR^2)(NR^{28}R^{29})$ where $R^{27}$, $R^{28}$ and $R^{29}$ independently represent hydrogen or alkyl, or $R^{27}$ and $R^{28}$ together are —$(CH_2)_n$— where n is 2 or 3 and $R^{29}$ is hydrogen or alkyl; or
—$COR^{30}$ where $R^{30}$ is alkyl, heteroalkyl, heterocyclylalkyl, aryl, aralkyl, heteroaryl or heteroaralkyl, preferably hydrogen, methyl, ethyl, 2-hydroxyethyl, 3-hydroxypropyl, 2-aminoethyl, 3-aminopropyl, 2-methylaminoethyl, 3-methylaminopropyl, 2-dimethylaminoethyl, 3-dimethylaminopropyl, 2-(morpholin-4-yl)ethyl, 3-(morpholin-4-yl)propyl, 2-(piperidin-1-yl)ethyl, 3-(piperidin-1-yl)propyl, 2-(piperazin-1-yl)ethyl, 3-(piperazin-1-yl)propyl, hydroxy, methoxy, 2-hydroxyethoxy, 3-hydroxy-propoxy, 2-methylaminoethoxy, 3-methylaminopropoxy, 2-dimethylaminoethoxy, 3-dimethylaminopropoxy, 2-(morpholin-4-yl)ethoxy, 3-(morpholin-4-yl)propoxy, 2-(piperidin-1-yl)ethoxy, 3-(piperidin-1-yl)propoxy, 2-(piperazin-1-yl)ethoxy or 3-(piperazin-1-yl)propoxy, more preferably hydrogen, hydroxy, methoxy, 2-(morpholin-4-yl)ethyl, 2-(morpholin-4-yl)ethoxy or 2-(piperidin-1-yl)ethyl; and $R^6$ is hydrogen, alkyl, alkoxy or halo, preferably hydrogen, methyl, methoxy, fluoro or chloro, most preferably hydrogen.

Within these preferred and more preferred groups, particularly preferred group of compounds is that wherein:

$R^1$ is a 4-pyridyl or 4-pyrimidinyl ring optionally substituted with a substituent selected from heteroalkyl, —NRR' (where R and R' are, independently of each other, hydrogen, alkyl, heterocyclylalkyl or heteroalkyl), —$NR^aC(O)R^b$ [where $R^a$ is hydrogen or alkyl and $R^b$ is hydrogen, alkyl or -(alkylene)-X where X is hydroxy, alkoxy, amino, alkylamino, dialkylamino, cycloalkyl, heterocyclyl, optionally substituted phenyl, imidazole or —$S(O)_nR'$ (where n is 0 to 2 and R' is alkyl)], —$NRSO_2R''$ [where R is hydrogen or alkyl and R" is alkyl or -(alkylene)-X where X is hydroxy, alkoxy, amino, alkylamino, dialkylamino or —$S(O)_nR'$ (where n is 0 to 2 and R' is alkyl)] or —OR (where R is alkyl or heteroalkyl), more preferably $R^1$ is a 4-pyridyl ring optionally substituted at the 2-position with a substituent selected from amino, acetylamino, methylamino, dimethylamino, methylsulfonylamino, 2-hydroxyethyl, 2-hydroxyethylamnino, 3-hydroxypropylamino, 2-aminoethylamino, 2-aminoethyl, 3-aminopropyl, 2-dimethylaminoethyl, methoxy, 2-hydroxyethoxy or 2-dimethylaminoethoxy; and $R^2$ is an aryl ring, preferably a phenyl ring optionally substituted with one or two substituents selected from alkyl, halo or —OR where R is alkyl, more preferably a phenyl ring substituted with one or two substituents selected from methyl, fluoro, chloro or methoxy, most preferably 4-fluorophenyl.

IV. A fourth more preferred group of compounds is that wherein:

Q is —O—; and

is a group represented by formula (W).

Within these preferred and more preferred groups, an even more preferred group of compounds is that wherein:

$R^6$ is hydrogen, alkyl, alkoxy or halo, preferably hydrogen, methyl, methoxy, fluoro or chloro, most preferably hydrogen.

Within these preferred and more preferred groups, particularly preferred group of compounds is that wherein:

$R^1$ is a 4-pyridyl or 4-pyrimidinyl ring optionally substituted with a substituent selected from heteroalkyl, —NRR' (where R and R' are, independently of each other, hydrogen, alkyl, heterocyclylalkyl or heteroalkyl), —$NR^aC(O)R^b$ [where $R^a$ is hydrogen or alkyl and $R^b$ is hydrogen, alkyl or -(alkylene)-X where X is hydroxy, alkoxy, amino, alkylamino, dialkylamino, cycloalkyl, heterocyclyl, optionally substituted phenyl, imidazole or —$S(O)_nR'$ (where n is 0 to 2 and R' is alkyl)], —$NRSO_2R''$ [where R is hydrogen or alkyl and R" is alkyl or -(alkylene)-X where X is hydroxy, alkoxy, amino, alkylamino, dialkylamino or —$S(O)_nR'$ (where n is 0 to 2 and R' is alkyl)] or —OR (where R is alkyl or heteroalkyl), more preferably $R^1$ is a 4-pyridyl ring optionally substituted at the 2-position with a substituent selected from amino, acetylamino, methylamino, dimethylamino, methylsulfonylamino, 2-hydroxyethyl, 2-hydroxyethylamino, 3-hydroxypropylamino, 2-aminoethylamino, 2-aminoethyl, 3-aminopropyl, 2-dimethylarninoethyl, methoxy, 2-hydroxyethoxy or 2-dimethylaminoethoxy; and $R^2$ is an aryl ring, preferably a phenyl ring optionally substituted with one or two substituents selected from alkyl, halo or —OR where R is alkyl, more preferably a phenyl ring substituted with one or two substituents selected from methyl, fluoro, chloro or methoxy, most preferably 4-fluorophenyl.

Exemplary particularly preferred compounds are:

3-(4-Fluorophenyl)-1-hydroxy-2-(pyridin-4-yl)-1H-pyrrolo [3,2-b]pyridine.

3-(4-Fluorophenyl)-1-methoxy-2-(pyridin-4-yl)-1H-pyrrolo [3,2-b]pyridine.

3-(4-Fluorophenyl)-2-(pyridin-4-yl)-1H-pyrrolo[3,2-b]
pyridine.
3-(4-Fluorophenyl)-2-[2-(2-hydroxyethylamino)pyridin-4-
yl]-1H-pyrrolo[3,2-b]pyridine.
3-(4-Fluorophenyl)-1-[2-(piperidin-1-yl)ethoxy]-2-
(pyridin-4-yl)-1H-pyrrolo[3,2-b]pyridine.
3-(4-Fluorophenyl)-2-(pyridin-4-yl)-1-[2-(morpholin-4-yl)
ethoxy]-1H-pyrrolo[3,2-b]pyridine.
3-(4-Fluorophenyl)-2-(pyridin-4-yl)- -[2-(morpholin-4-yl)
ethyl]-1H-pyrrolo[3,2-b]pyridine.
3-(4-Fluorophenyl)-1-[2-(piperidin-1-ylethyl]-2-(pyridin-4-
yl)-1H-pyrrolo[3,2-b]pyridine.
7-(4-Fluorophenyl)-6-(pyridin-4-yl)-5H-pyrrolo[2,3-b]
pyrazine.
6-(2-Acetylaminopyridin-4-yl)-7-(4-fluorophenyl)-5H-
pyrrolo[2,3-b]pyrazine.

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif., USA), Emnka-Cherie, or Lancaster (Windham, N.H., USA) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989), *Organic Reactions*, Volumes 1–40 (John Wiley and Sons, 1991), *March's* Advanced Organic Chemistry, (John Wiley and Sons, 4th Edition), and *Larock's* Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Preparation of compounds of Formula (I)

Schemes A–M describe methods to synthesize compounds of Formula (I).

Scheme A

Compounds of Formula (I) where - - - - - - is between B and —CR$^1$—, Q is —NR$^4$—,

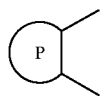

is a group of formula (S) or (T) and other groups are as defined in the Summary of the Invention are prepared as described below.

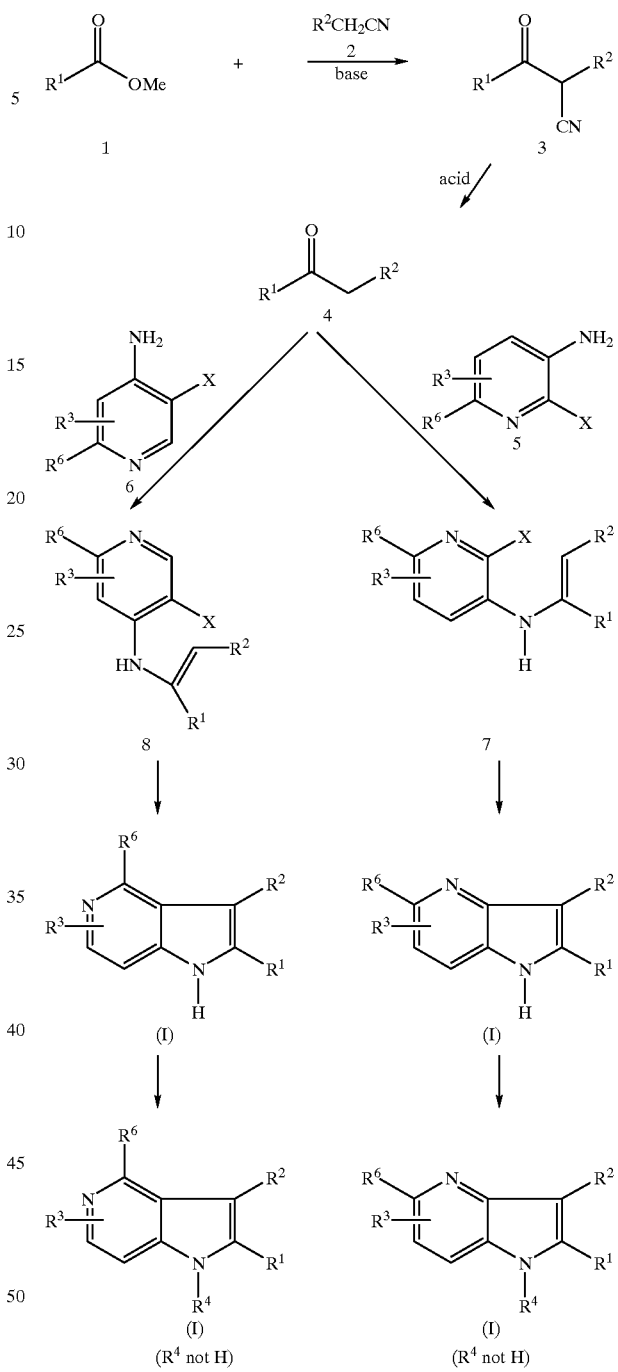

Reaction of an ester of formula 1 with an acetonitrile derivative of formula 2 in the presence of a suitable base such as sodium ethoxide or potassium t-butoxide, each in its respective alcohol as solvent gives a β-keto-acetonitrile intermediate of formula 3 ((see., Ivan Lantos, I. et al. *J. Org. Chem.* 53, 4223–4227 (1988)). Alternatively, the reaction can be carried out in the presence of lithium diisopropylamide or lithium hexamethyldisilazane in tetrahydrofuran.

In general, compounds of formula 1 are commercially available or they can be prepared by methods well known in the art. For example, methylisonicotinate is commercially available. Others can be prepared from suitable starting materials such as 2-chloropyridine-4-carboxylic acid, 3- or 4-quinolinecarboxylic acid, 2-pyrazinecarboxylic acid, 4-methyl-5-pyirnidinecarboxylic acid, 4-pyrimidinecarboxylic acid, 2-pyrazinecarboxylic acid under standard esterification reaction conditions.

Compounds of formula 2 such as 2-phenylacetonitrile, 4-fluorophenylacetonitrile, pyridylacetonitrile, and the like are commercially available.

Hydrolysis and decarboxylation of the cyano group in 3 in a suitable aqueous acid such as hydrobromic acid provides a ketone of formula 4. Alternatively, a compound of formula 4 can be prepared directly, by reacting the sodium salt of an acid of formula $R^1 COO^- Na_g^+$ with a Grignard reagent of formula $R^2CH_2MgX$ (where X is halo).

Condensation of 4 with a 3-aminopyridine of formula 5 or a 4-aminopyridine of formula 6 where X is a halo group (e.g., chloro, bromo or iodo) gives an enamine of formula 7 or 8 respectively. The condensation reaction is carried out in the presence of a catalytic amount of an acid such as p-toluenesulfonic acid in an aromatic hydrocarbon as a solvent e.g., toluene or xylene.

Compounds of formula 5 are either commercially available or they can be prepared by methods well known in the art. For example, 3-amino-2-chloropyridine is commercially available. 3-amino-2-chloro-6-bromopyridine and 3-amino-2-bromo-6-methoxypyridine can be prepared by following the procedure described in Proudfoot, J. R., et al., *J. Med. Chem.*, 38(24), 4830, (1995). 3-amino-2,6-dichloro-4-methylpyridine can be prepared by following the procedure described in Grozinger, K. G., et al., *J. Heterocycl. Chem.*, 32(1), 259, (1995). 3-amino-2,5-dichloropyridine can be prepared by first converting 5-chloro-3-nitro-2-pyridinone to 2,5-dichloro-3-nitropyridine as described in *J. Heterocycl. Chem.*, 31(1), 73, (1994)) followed by reduction of the nitro group as described in Berrie et al., *J. Chem. Soc.*, 2042 (1952).

Compounds of formula 6 such as 4-amino-3-chloropyridine and 4-amino-3-chloro-6-methylpyridine can be prepared by following the procedures described in Sugasawa, T., et al. *J. Am. Chem. Soc.*, 4842–4851 (1978) and Turner J. A., *J. Org. Chem.*, 48, 3401–3408 (1983) respectively. 4-amino-3-fluoro-6-methoxypyridine can be prepared by following the procedure described in Nesnow, H. *J. Heterocycl. Chem.*, 12,941, (1975).

Cyclization of the enamine 7 or 8 provides the 1H-pyrrolo [3,2-b]pyridine or the 1H-pyrrolo[3,2-c]pyridine of Formula (I), respectively. The cyclization reaction is carried out in the presence of a palladium (II) catalyst such as dichlorobis (triphenylphosphine)palladium (II) in the presence of a tertiary amine such as Dabco™ and in an inert organic solvent such as dimethylformamide ((see., Chen, C. et al. *J. Org. Chem.*, 62, 2676–2677 (1997) and Sakamoto, T. et al. *Synthesis*, 215 (1990)).

A compound of Formula (I) can be converted, if desired, to other compounds of Formula (I). For example, (i) A 1H-pyrrolo-[3,2-b]pyridine or a 1H-pyrrolo-[3,2-b] pyridine of Formula (I), where $R^4$ is hydrogen can be converted to its corresponding compound of Formula (I) where $R^4$ is not hydrogen by reacting it with an alkylating agent $R^4Y$ where Y is a leaving group under alkylating conditions (such as halo, mesylate, tosylate and the like) or an acylating $R^4COL$ where L is leaving group under acylating reaction conditions such as halo (preferably chloro). The reaction is carried out in the presence of a strong base such as sodium hydride and in an aprotic organic solvent such as tetrahydrofuran, dimethylformamide, and the like.

(ii) A 1H-pyrrolo[3,2-b]pyridine or a 1H-pyrrolo-[3,2-c] pyridine of Formula (I) can be substituted at the 7-position ($R^3$=7-position) using an ortho lithiation protocol. Thus, protection of the N1 nitrogen with an ortho directing protecting group such as trimethylsilylethoxymethyl (SEM), tert-butoxycarbonyl or N-tert-butyl carbamoyl, followed by lithiation with a strong base such as lithium diisopropylamide, lithium 2,2,6,6-tetramethylpiperidine, n-butyllithium or tert-butyllithium in tetrahydrofuran or diethylether would lithiate the 7-position of the pyrrolo[3, 2-b]pyridine/pyrrolo-[3,2-c]pyrdine ring. Treatment of the 7-lithio species with an electrophile such as alkyl disulfide, iodine, dimethylformamide, carbon dioxide will give a corresponding pyrrolo[3,2-b]pyridine/pyrrolo[3,2-c]pyridine of Formula (I) substituted at the 7-position with an iodo, formyl or carboxy group respectively ((see Gharpure, M.; et al. *Synthesis*, 12, 1079–82 (1991)).

Scheme B

Scheme B describes an alternative method to synthesize a compound of Formula (I) where - - - - - - is between B and —$CR^1$—, Q is —$NR^4$—,

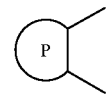

is a group of formula (S) or (T) and other groups are as defined in the Summary of the Invention.

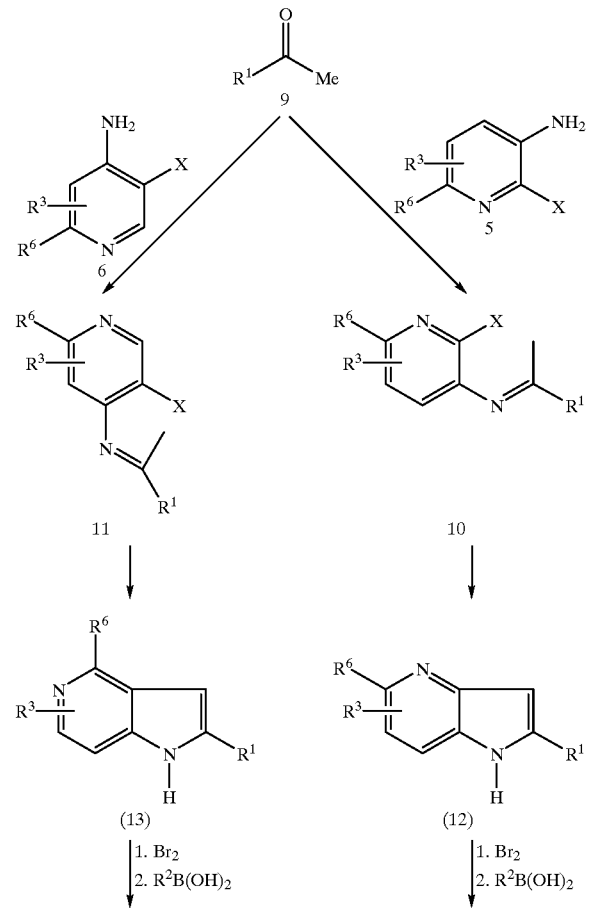

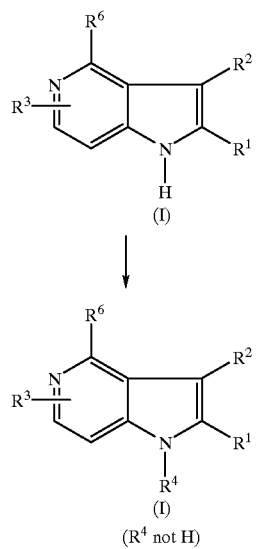
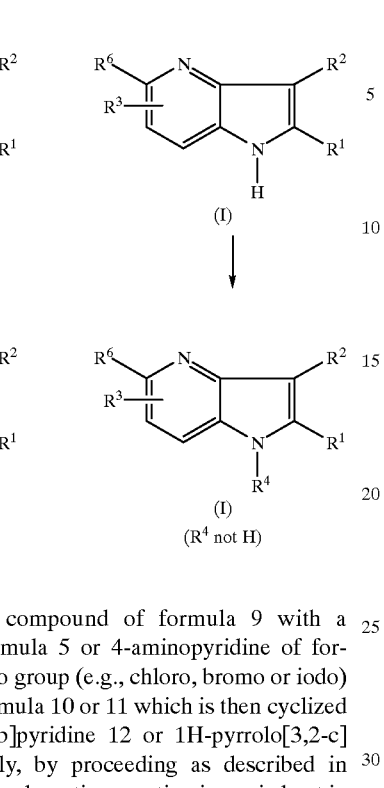
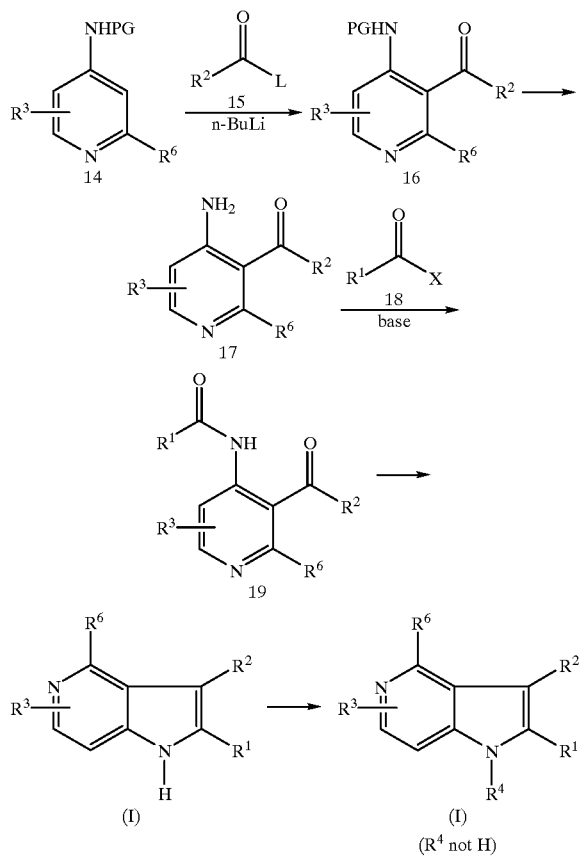

Condensation of a compound of formula 9 with a 3-aminopyridine of formula 5 or 4-aminopyridine of formula 6 where X is a halo group (e.g., chloro, bromo or iodo) gives an enamine of formula 10 or 11 which is then cyclized to the 1H-pyrrolo[3,2-b]pyridine 12 or 1H-pyrrolo[3,2-c] pyridine 13 respectively, by proceeding as described in Scheme A above. The condensation reaction is carried out in the presence of a suitable base such as sodium hydride and in an aprotic solvent e.g., tetrahydrofuran or dimethylformamide.

Bromination of 12 or 13 with bromine in dimethylformamide gives the corresponding 3-bromo derivative which upon treatment with boronic acid of formula $R^2B(OH)_2$ (where $R^2$ is as defined in the Summary of the Invention) under Suzuki coupling reaction conditions ((see., Miyaura, N. *Chem. Commun.*, 866, (1979)) gives 1H-pyrrolo[3,2-b] pyridine or 1H-pyrrolo[3,2-c]pyridine of Formula (I) respectively.

A 1H-pyrrolo(3,2-b]pyridine or 1H-pyrrolo[3,2-c] pyridine of Formula (I) where $R^3$, $R^4$ and $R^6$ are hydrogen can be converted to the corresponding 1H-pyrrolo[3,2-b] pyridine or 1H-pyrrolo[3,2-c]pyridine of Formula (I) where $R^3$, $R^4$ and $R^6$ are other than hydrogen, if desired, by following the procedures described in Scheme A above.

Scheme C

Scheme B describes an alternative method to synthesize a compound of Formula (I)

where - - - - - - is between B and —$CR^1$—, Q is —$N^4$—,

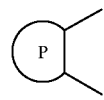

is a group of formula (T) and other groups are as defined in the Sunmmary of the Invention.

Reaction of a 4-aminopyridine of formula 14 where PG is an ortho-directing amino protecting group such as tert-butoxycarbonyl, pivaloyl or benzoyl, preferably pivaloyl, with a compound of formula 15, where L is a leaving group under acylating conditions [e.g., alkoxy (preferably methoxy or ethoxy), dialkylamino, halo (preferably chloro), or preferably N,O-dimethylhydroxylamino] gives a 3-acyl-4-aminopyridine derivative of formula 16. The reaction is carried out in the presence of a strong base such as n-butyllithium in an aprotic polar organic solvents such as diethyl ether, tetrahydrofuran, and the like ((see., Sugasawa, T. et al. *J. Am. Chem. Soc.* 4842–4851 (1978)). 4-Aminopyridine is commercially available.

Deprotection of the amino group, followed by treatment of the resulting 4-aminopyridine 17 with an acyl halide of formula 18 in the presence of a non-nucleophilic base (such as triethylamine, pyridine and the like) gives a 4-amido-3-acylpyridine of formula 19. The deprotection is carried out under acidic hydrolysis reaction conditions. Suitable acids are inorganic acids such as hydrochloric acid.

Compounds of formula 18 where X is chloro can be prepared from suitable starting materials such as 2-chloropyridine-4-carboxylic acid, 3- or 4-quinolinecarboxylic acid, 2-pyrazinecarboxylic acid, 4-methyl-5-pyrimidinecarboxylic acid, 4-pyrimidinecarboxylic acid, 2-pyrazinecarboxylic acid by treatment with a chlorinating agent such as thionyl chloride, oxalyl chloride, and the like.

The 4-amido-3-acylpyridine 19 is converted to the 1H-pyrrolo[3,2-c]pyridine of Formula (I) ($R^4$ is hydrogen) by following the procedure described in Furstner, A et al, *J. Org. Chem.*, 59, 5215–5229, (1994).

A compound of Formula (I) where $R^4$ is hydrogen can be converted to other compounds of Formula (I) where $R^4$ is not hydrogen as described in Scheme A above.

Scheme D

Compounds of Formula (I) where - - - - - - is between B and —CR$^1$—, Q is —NOR$^5$—,

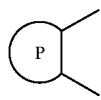

is a group of formula (S) or (T) and other groups are as defined in the Summary of the Invention are prepared as described below.

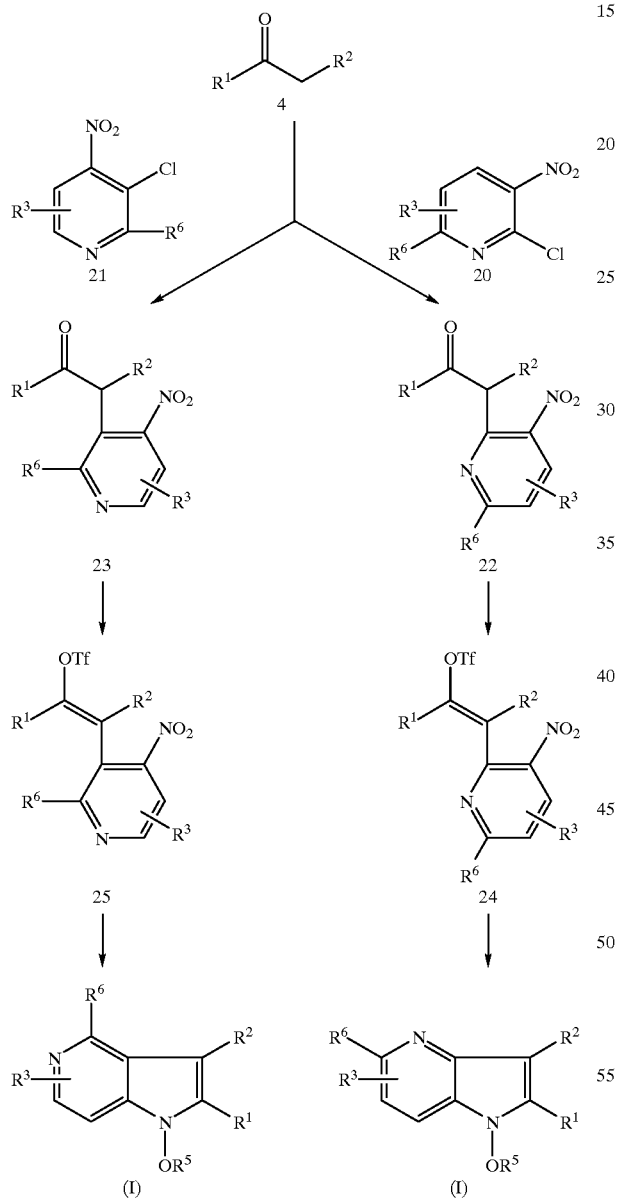

Reaction of a ketone of formula 4 with a 2-chloro-3-hitropyridine 20 or a 3-chloro-4-nitropyridine 21 under nucleophilic substitution reaction conditions gives an α-(3-nitro-2-pyridyl)ketone of formula 22 or α-(4-nitro-3-pyridyl)ketone of formula 23 respectively. The reaction is carried out in the presence of a strong non-nucleophilic base such as sodium hydride in an aprotic organic solvent such as dimethylformamide, and the like.

Compounds of formula 20 and 21 are either commercially available or they can be prepared by methods known in the art. For example, 2-chloro-3-nitropyridine, 3-chloro-4-nitropyridine, 2-chloro-4-methyl-3-nitropyridine, 2-chloro-6-methoxy-3-nitropyridine are commercially available. Compounds such as 2,5-dichloro-3-nitropyridine, 2-chloro-5,6-dimethyl-3-nitropyridine and 3-fluoro-4-nitro-2,6-dimethylpyridine can be prepared by the procedures described in Berrie et al., *J. Chem. Soc.*, 2042, (1952), Wai, J. S., et al., *J. Med. Chem.*, 36(2), 249, (1993), and Markley, E., *J. Med. Chem.*, 16, 297, (1973), respectively Conversion of 22 or 23 to the corresponding triflate derivatives 24 or 25, followed by nitro group reduction and concomitant ring cyclization gives the 1-hydroxy-1H-pyrrolo[3,2-b]pyridine or 1-hydroxy-1H-pyrrolo[3,2-c] pyridine (1) (R$^5$=H), respectively. The triflate reaction is carried out by reaction 22 or 23 with triflic anhydride in the presence of a non-nucleophilic base such as triethylarine, pyridine, preferably pyridine. Suitable solvents are halogenated hydrocarbons such as dichloromethane, chloroform, and the like. The reductive cyclization reaction is carried out using tin (II) chloride dihydrate or titanium (m) chloride in solvents such as ethanol or ethyl acetate or it can be carried out under standard hydrogenolysis reaction conditions.

Alternatively, the 1-hydroxy-1H-pyrrolo[3,2-b]pyridine and 1-hydroxy-1H-pyrrolo[3,2-c]pyridine (I) can be prepared directly from 22 and 23 respectively, under the same ring cyclization reaction conditions without proceeding through the triflate intermediate.

A compound of Formula (I) where R$^5$ is hydrogen can be converted its corresponding compounds of Formula (I) where R$^5$ is other than hydrogen by reacting it with an alkylating agent R$^5$Y, as described in Scheme A above.

Scheme E

Compounds of Formula (I) where - - - - - - is between B and —CR$^1$—, Q is —O—,

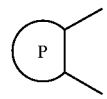

is a group of formula (S) and other groups are as defined in the Summary of the Invention are prepared as described below.

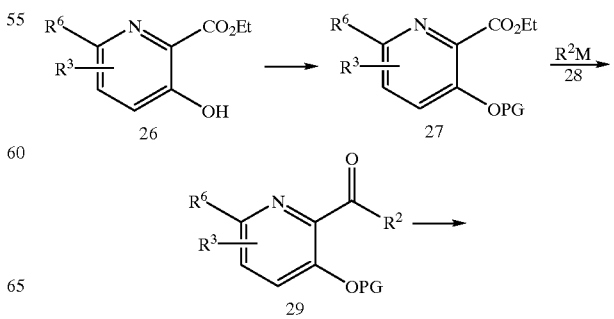

-continued

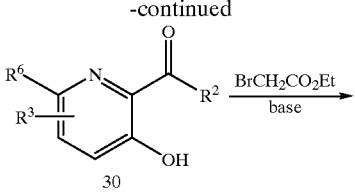

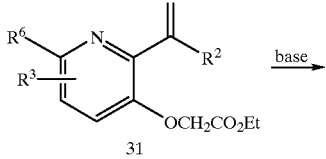

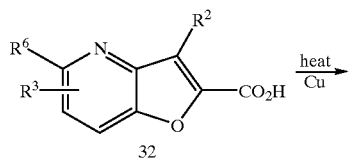

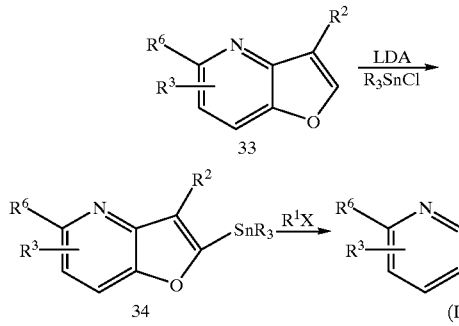

Protection of the hydroxy group in an ethyl 3-hydroxy-2-picolinate of formula 26 with a suitable protecting group (such as tert-butyldimethylsilyl, and the like) followed by treatment with an organometallic reagent such as an organolithium or Grignard reagent of formula 28 under nucleophilic substitution reaction conditions gives a 2-ketopyridine of formula 29. The reaction with the organometallic reagent is carried out in an inert organic solvent such as diethyl ether or tetrahydrofuran, preferably diethyl ether. Ethyl 3-hydroxy-2-picolinate is prepared from commercially available 3-hydroxypicolinic acid by methods well known in the art.

Removal of the O-protecting group in 29 gives a 2-keto-3-hydroxypyridine of formula 30. The reaction conditions used for the deprotection depend on the nature of the protecting group. For example, if tert-butyldimethylsilyl is used then it is removed with tetrabutylammonium fluoride in an ethereal solvent such as tetrahydrofuran. For other suitable O-protecting groups see T. W. Greene, "Protective Groups in Organic Synthesis," Wiley, New York (1991) and J. F. McOmie, "Protective Groups in Organic Chemistry," Plenum Press, London (1973).

Reaction of 30 with ethyl bromoacetate in the presence of a non-nucleophilic base such as sodium hydride in a suitable organic solvent such as tetrahydrofuran gives a compound of formula 31. Treatment of 31 with base such as sodium ethoxide in ethanol, followed by thermolysis of the resulting 2-carboxyfuro[3,2-b]pyridine of formula 32 gives furo[3,2-b]pyridine of formula 33 ((see., Shiotani, S., and Moriata, H. *J. Heterocyclic Chem.*, 23, 665 (1986))

o-Lithiation of 33 with a base such as lithium diisopropylaride or n-butyllithium, followed by treatment with an organotin reagent such as tributyltin chloride gives.34 Coupling of 34 with an organic halide of formula $R^1X$ (where X is chloro, bromo or iodo) then provides furo[3,2-b]pyridine of Formula (I). The reaction is carried out in the presence of a Pd(II) catalyst such as dichlorobis(triphenylphosphine) palladium (II) in inert organic solvent such as dimethylformamide or xylenes.

Substituting ethyl 3-hydroxy-2-picolinate 26 with ethyl 4-hydroxynicotinate ((see., Bojarska-Dahlig, Nantka-Namirski, *Rocz. Chem.*, 29, (1955)) and proceeding as described in Scheme E above, gives furo[3,2-c]pyridine of Formula (I).

Scheme F

A compound of Formula (I) where - - - - - - is between B and —$CR^1$—, Q is —S—,

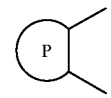

is a group of formula (S) and other groups are as defined in the Summary of the Invention are prepared as described below.

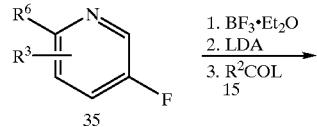

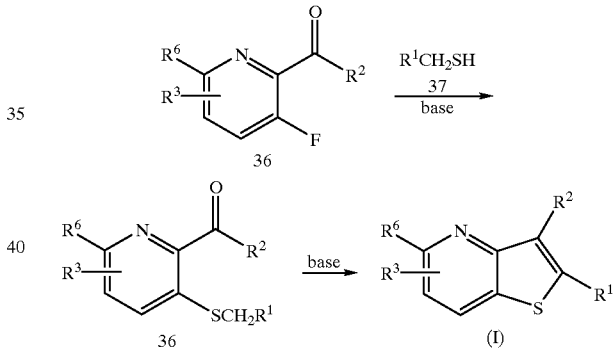

Reaction of a 3-fluoropyridine of formula 35 with a compound of formula 15 where L is a leaving group under acylating conditions [e.g., alkoxy (preferably methoxy or ethoxy), dialkylamino, halo (preferably chloro), or preferably N,O-dimethylhydroxylamino] gives a 2-acyl-3-fluoropyridine of formula 36. The reaction is carried out in the presence of a Lewis acid such as boron trifluoride and a strong base such as lithium diisopropylamide and in an aprotic polar organic solvents such as diethyl ether, tetrahydrofuran, and the like ((see., Kessar, S. V. et al. *J. Chem. Soc. Chem. Commun.* 570 (1991) and Vedejs, E. and Chen, X. *J. Am. Chem. Soc.* 118, 1809–1810 (1996)).

Nucleophilic substitution of the fluoro group in 36 by a thiol reagent of formula 37 gives a compound of formula 38. The reaction is carried out in the presence of a base such as sodium hydride in a suitable solvent such as tetrahydrofuran. A thiol reagent such as (4-pyridyl)methylthiol can be prepared by the procedure described in Barnes, J. H., *J. Med. Chem.*, 23(3), 211, (1988).

Cyclization of 38 to thieno[3,2-b]pyridine of Formula (I) is achieved upon heating 38 in an alcoholic solvent such as ethanol in the presence of a base such as sodium ethoxide.

Substituting 3-fluoropyridine 35 with 4-fluoropyridine and following the procedure in Marsais, F., et al., *J. Heterocycl. Chem.*, 25(1), 81, (1988) gives 3-acyl-4-fluoropyridine which can then be converted to thieno[3,2-c]pyridine of Formula (I) by proceeding as described in Scheme F above.

Scheme G

A compound of Formula (I) where - - - - - - is between B and —CR$^1$—, Q is —NR$^4$—,

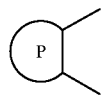

is a group of formula (U) and other groups are as defined in the Summary of the Invention can be prepared as described below.

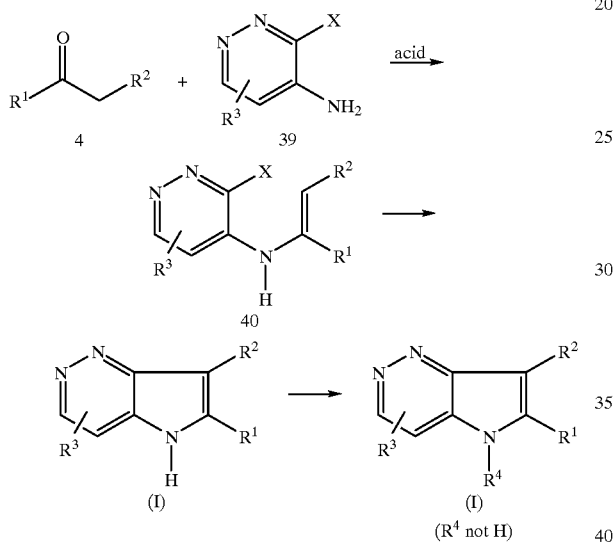

Condensation of a ketone of formula 4 with a 4-aminopyridazine of formula 39 where X is a halo group (e.g., chloro, bromo or iodo) gives an enamine of formula 40. The condensation reaction is carried out in the presence of a catalytic amount of an acid such as p-toluenesulfonic acid or a Lewis acid such as aluminum chloride in an aromatic hydrocarbon as a solvent e.g., toluene or xylene. Compound 40 is then converted to 5H-pyrrolo[3,2-c]pyridazine of Formula (I) by proceeding as described in Scheme A above.

Compounds of formula 39 can be prepared by methods well known in the art. For example, 4-amino-3-chloropyridazine is prepared from commercially available 4,5-dichloropyridaz-3-one by first converting it to 4-chloro-5-hydrazinopyridaz-3-one by treatment with hydrazine under the reaction conditions described in *Yakugaku Zasshi*, 85, 344 (1965).

Removal of the hydroazino group with copper sulfate or silver oxide in aqueous medium gives 4-chloropyridaz-3-one which is then converted to 4-amino-3-chloropyridazine by following the procedure described in Klinge, D. E., *Recueil des travaus chimiques des Pays-Bas*, 93(8), 236–239, (1974).

Scheme H

A compound of Formula (I) where - - - - - - is between B and —CR$^1$—, Q is —NR$^4$—,

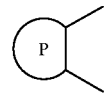

is a group of formula (V) and other groups are as defined in the Summary of the Invention can be prepared as described below.

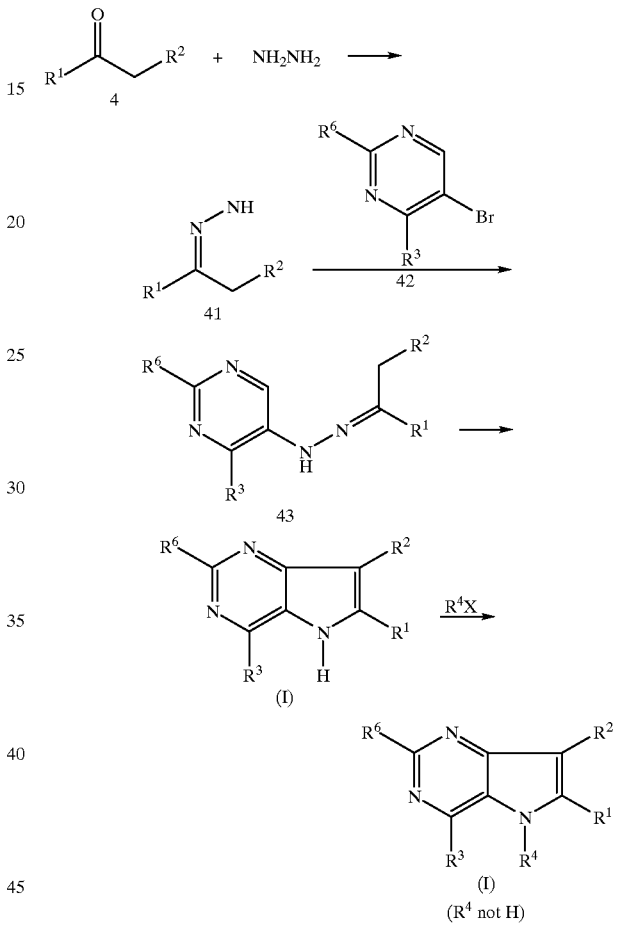

Condensation of a compound of formula 4 with hydrazine gives a hydrazone of formula 41. The reaction is carried out in the presence of a catalytic amount of an acid such as p-toluenesulfonic acid in an alcoholic solvent such as ethanol. Reaction of 41 with a pyrimidine of formula 42 provides a compound of formula 43 which is then converted to 5H-pyrrolo[3,2-d]pyrimidine of Formula (I) by heating 43 in high boiling solvent such as diethylene glycol.

A 5H-pyrrolo-[3,2-d]pyrimidine of Formula (I) where R$^3$, R$^4$ and R$^6$ are hydrogen can be converted to the corresponding 5H-pyrrolo[3,2-d]pyrimidine of Formula (I) where R$^3$, R$^4$ and R$^6$ are other than hydrogen, if desired, by following the procedures described in Scheme A above.

Scheme I

A compound of Formula (I) where - - - - - - is between B and —CR$^1$—, Q is —NR$^4$—,

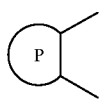

is a group of formula (W) and other groups are as defined in the Summary of the Invention are prepared as described below.

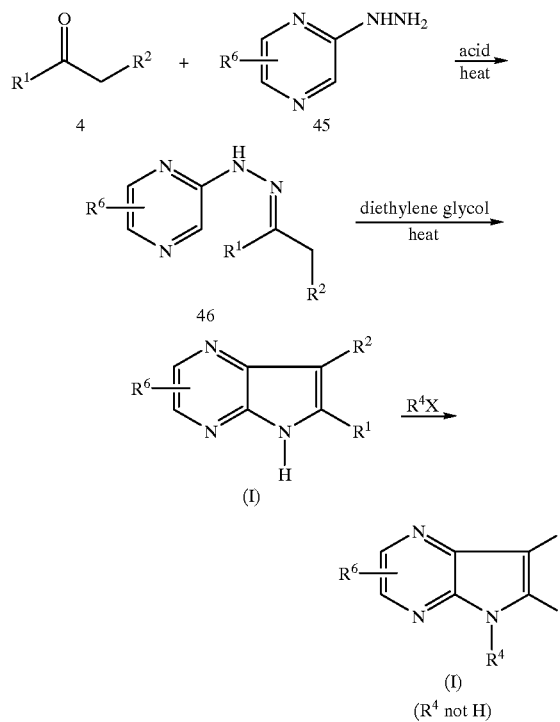

Condensation of a ketone of formula 4 with a 2-hydrazinopyrazine of formula 45 in the presence of a catalytic amount of an acid such as p-toluenesulfonic acid gives a hydrazone of formula 46 ((see, *J. C. S. Perkin I,* 1361–1363, (1976)). Suitable solvents for the reaction are aromatic hydrocarbons such as toluene. Compounds of formula 4 are prepared as described in Scheme A. A compound of formula 45 where $R^6$ is hydrogen is prepared by reacting chloropyrazine with hydrazine under conditions well known in the art ((see., *Euro. J. Med. Chem.,* 24(3), 249–57 (1989) and *J. Heterocyclic Chem.,* 11, 697–701, (1974)).

Conversion of 46 to a 5H-pyrrolo[2,3-b]pyrazine of Formula (I) where $R^4$ is hydrogen is achieved by heating 46 in high boiling solvent such as diethylene glycol. For other suitable cyclization reaction conditions see R. J. Sundberg, "*Indoles*," Academic Press, San Diego, Calif., 1996, p 55.

A compound of Formula (I) where $R^4$ is hydrogen can be converted to other compounds of Formula (I) where $R^4$ is not hydrogen as described in Scheme A above.

Scheme J

A compound of Formula (I) where - - - - - - is between B and —$CR^1$—, Q is O or S,

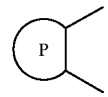

is a group of formula (W) and other groups are as defined in the Summary of the Invention are prepared as described below.

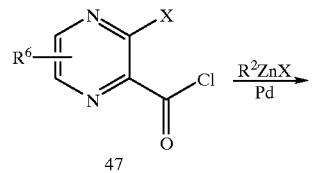

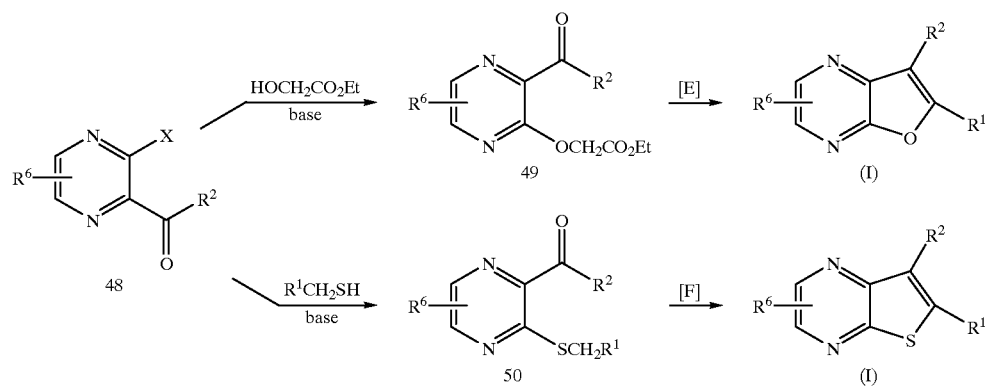

Reaction of a 3-pyrazinecarbonyl chloride of formula 47 (where X is a halo group such as chloro or bromo) with an organozinc reagent of formula R₂ZnX under the reaction conditions such as those described in Negishi, E. et al., *Tet. Lett.*, 24(47), 5181, (1983) gives a 2-ketopyrazine of formula 48. 2-chloro-3-pyrazinecarbonyl chlorides can be prepared by following the procedure described in Friary, R. J., *Tetrahedron*, 49(33), 7179 (1993).

Nucleophilic substitution of the halo group in 48 by ethyl glycolate or a thiol reagent of formula $R^1CH_2SH$ gives a compound of formula 49 or 50 respectively. The reaction is carried out in the presence of a base such as sodium hydride in a suitable solvent such as tetrahydrofuran A compound of formula 49 or 50 is then converted to a furo[2,3-b]pyrazine or a thieno[2,3-b]pyrazine of Formula (I) respectively, by proceeding as described in Scheme E or F above.

Substituting 2-chloro-3-pyrazinecarbonyl chloride 47 with 5-chloro-4-pyrimidinecarbonyl chloride (see., U.S. Pat. No. 4,110,450) and following the procedures described above gives furo[3,2-d]pyrimidine or a thieno[3,2-d] pyrimidine of Formula (I), respectively.

Scheme K

A compound of Formula (I) where - - - - - - is between Q and —$CR^1$—, B is nitrogen,

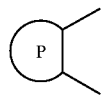

is a group of formula (S) and other groups are as defined in the Summary of the Invention are prepared as described below.

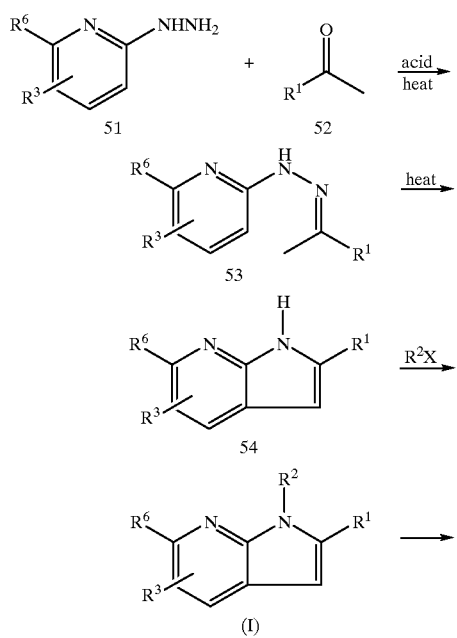

-continued

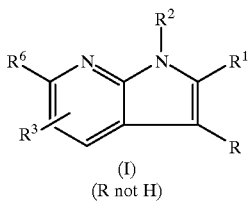

(I)
(R not H)

Condensation of a 2-hydrazinopyridine of formula 51 with a ketone of formula 52 in the presence of a catalytic amount of an acid such as p-toluenesulfonic acid gives a hydrazone of formula 53. Suitable solvents for the reaction are aromatic hydrocarbons such as toluene.

Compounds of formula 51 are either commercially available or they can be prepared by methods known in the art. For example, 2-hydrazinopyridine is commercially available. 3-chloro-2-hydrazinopyridine can be prepared by heating 2,3-chloropyridine with hydrazine under conditions well known in the art ((see., *Euro. J. Med. Chem.*, 24(3), 249–57 (1989)). Compounds of formula 52 such as 2-, 3-, 4-acetylpyridine, 2-acetylpyrazine are commercially available.

Conversion of 53 to a 1H-pyrrolo[2,3-b]pyridine of formula 54 is achieved by heating 53 in high boiling solvent such as diethylene glycol. For other suitable cyclization reaction conditions see., R. J. Sundberg, "*Indoles*," Academic Press, San Diego, Calif., 1996, p 55.

Conversion of 54 to a compound of Formula (I) where R is hydrogen is achieved by reacting 54 with an aryl halide of formula $R^2X$ (where $R^2$ is as defined in the Surnrnay of the Invention and X is a halo group) under the reaction conditions such as those described in Smith III, W. J. and Sawyer, J. S., *Tet. Lett.*, Vol. 37(3), 299–302 (1996) or Zhang, Lin-hua et al., *Tet. Lett.*, Vol. 36(46), 8387–8390, (1995).

A compound of Formula (I) where R is hydrogen can be converted to the corresponding compound of Formula (I) where R is other than hydrogen by following the procedures described in R. J. Sundberg, "*Indoles*," Academic Press, San Diego, Calif., 1996, p 105–118.

Substituting 2-hydrazinopyridine 51 with 4-hydrazinopyrimnidine, 3-hydrazinopyridazine or 2-hydrazinopyrazine and following the procedure described above gives 7H-pyrrolo[2,3-d]pyrimidine, 7H-pyrrolo[2,3-c]pyridazine or 5H-pyrrolo[2,3-b]pyrazine respectively.

4-Hydrazinopyrimidine and 3-hydrazinopyridazine can be prepared as described in Barlin, G. B., et al., *J. Chem. Soc., Perkin Trans.* 1 (1972) and Pinza, M. et al., *Farmaco*, 49(11), 683–92 (1994) respectively.

Scheme L

An alternative route for preparing a compound of Formula (I) where - - - - - - is between Q and —$CR^1$—, B is nitrogen,

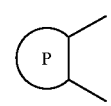

is a group of formula (S) and other groups are as defined in the Summary of the Invention is described below.

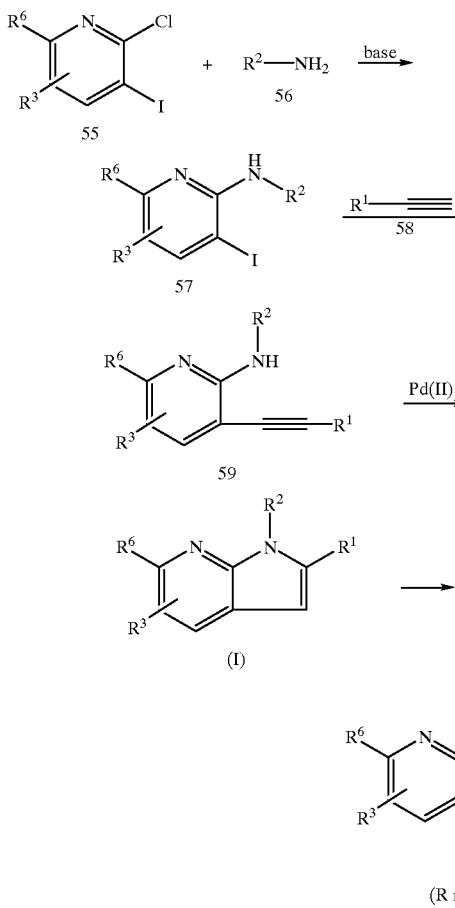
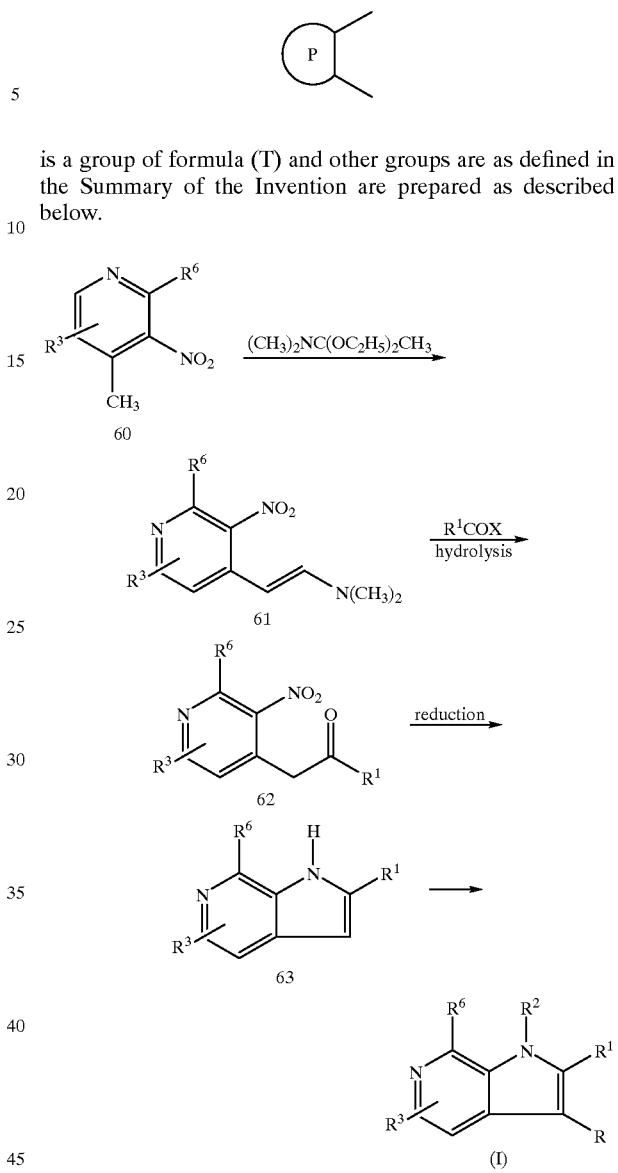

is a group of formula (T) and other groups are as defined in the Summary of the Invention are prepared as described below.

Reaction of a 2-chloro-3-iodopyridine of formula 55 with an amine of formula 56 gives a 2-amino-3-iodopyridine of formula 57. The reaction is carried out in the presence of a non-nucleophilic base such as pyridine. 2-chloro-3-iodopyridine can be prepared by the procedures described in Guillier, F., et al, *Tet. Lett.*, 35(35), 6489, (1994) and Rocca, P. et al., *Tetrahedron*, 49(1), 49, (1993). Compounds of formula 56 such as aniline, 4-fluoroaniline, 4-methylaniline are commercially available.

Coupling of 57 with an alkyne of formula 58 gives 3-alkynyl-2-aminopyridine of formula 59 which is then cyclized to 1H-pyrrolo[2,3-b]pyridine of formula (I). The alkynyl coupling reaction is carried under the reaction conditions such as those described in de Souza, P. T., *Quim. Nova*, 19(4), 377 (1996). The cyclization reaction is carried out in the presence of a palladium (II) catalyst and in an inert organic solvent such as acetonitrile or tetrahydrofuran ((see., Iritani, K. et al. *Tet. Lett.*, 29(15), 1799 (1988)).

Compounds of formula 58 such as 2-ethynylpyridine, 4-ethynylpyridine can be prepared by the procedure described in Yashima, E. et al., *Japan Chirality*, 9(5/6), 593–600 (1997).

Scheme M

Compounds of Formula (I) where - - - - - - is between Q and —$CR^1$—, B is nitrogen, Reaction of a 4-methyl-3-nitropyridine of formula 60 with N,N-dimethylformamide diethyl acetal in N,N-dimethylformamide gives a 4-(2-dimethylaminoethylene)-3-nitropyridine of formula 61. Treatment of 61 with an acyl halide of formula $R^1COX$ (where $R^1$ is as defined in the Summary of the Invention and X is a halo group) gives a ketone of formula 62 which upon reduction either catalytically or with sodium hydrosulfite provides a 2-substituted pyrrolo[2,3-c]pyridine of formula 63. Conversion of 60 to 63 is carried out under the reaction conditions described in Garcia, E. E and Fryer, R. I., *J. Heterocyclic Chem.*, 11, 219, (1974).

A compound of formula 63 is then converted to a compound of Formula (I) as described in Scheme K above.

Additional Processes

Compounds of Formula (I) can also be prepared by modification of a group present on a corresponding compound of Formula (I) by known procedures. Some examples of such procedures are described below:

(i) A compound of Formula (I) where $R^6$ is alkoxy can be prepared from a corresponding compound of Formula (I) where $R^6$ is chloro or bromo by treating it with an alkoxide under known reaction conditions. De-alkylation of an alkoxy substituent provides a corresponding compound of Formula (I) where $R^6$ is hydroxy which can then be converted to a corresponding compound of Formula (I) where $R^6$ is heteroalkyloxy or heterocyclylalkyloxy by treatment with the appropriate alkylating agent. Alternatively, the heteroalkyloxy can be put on by following literature procedures described in *J. Org. Chem.*, 61, 7240, (1996) and *Tetrahedron*, 44, 91, (1988) respectively.

(ii) Compounds of Formula (I) where $R^6$ is monosubstituted amino or disubstituted amino can be prepared by reacting the corresponding compound of Formula (I) where $R^6$ is chloro or bromo with a primary or secondary amine either in the presence or absence of a palladium catalyst as described in Wagaw, S; et al. *J. Org. Chem.* 61(21), 7240 (1996) and Wolfe, J. P.; et al. *Tet. Lett.* 38(36), 6367 (1997).

(iii) Compounds of Formula (I) where $R^6$ is cyano can be prepared by reacting the corresponding compound of Formula (I) where $R^6$ is chloro or bromo with copper cyanide in N,N-dimethylformamide or dimethyl sulfoxide as described in *Heterocycles*, 41 (12), 2799, (1995). Alternatively, it can be done with potassium cyanide in the presence of nickel or zinc catalyst as described in *Bull. Chem. Soc. Jpn.*, 66(9), 2776, (1993).

(iv) Compounds of Formula (I) where $R^6$ is alkyl can be prepared by reacting the corresponding compound of Formula (I) where $R^6$ is chloro or bromo with alkyllithium or an alkyltin reagent in the presence of a palladium catalyst.

It will be recognized by one skilled in the art that these transformation are not limited to the $R^6$ position but may be carried out at other positions in the compound of Formula (I).

Preparation of 7-(4-fluorophenyl)-6-[2-(3-hydroxypropylamino)pyridin-4-yl]-5H-pyrrolo[2,3-b]pyrazine from 7-(4-fluorophenyl)-[12-bromopyridin-4-yl]-5H-pyrrolo[2,3-b]pyrazine is described in Example 12.

UTILITY, TESTING, AND ADMINISTRATION

Utility

The compounds of Formula (I) are p38 MAP kinase and JNK inhibitors and therefore compounds of Formula (I) and compositions containing them are useful in the treatment of diseases such as rheumatoid arthritis, osteoarthritis, spondylitis, bone resorption diseases, sepsis, septic shock, toxic shock syndrome, endotoxic shock, tuberculosis, atherosclerosis, diabetes, adult respiratory distress syndrome, chronic pulmonary inflammatory disease, fever, periodontal diseases, ulcerative colitis, pyresis, Alzheimer's and Parkinson's diseases.

Testing

The ability of the compounds of Formula (I) to inhibit p38 MAP kinase was demonstrated by the in vitro assay described in Example 20. The ability of the compounds of Formula (I) to inhibit the release of TNF-α was demonstrated by the in vitro and the in vivo assays described in detail in Examples 21 and 22, respectively.

Administration and Pharmaceutical Compositions

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula (I) may range from approximately 0.1–50 mg per kilogram body weight of the recipient per day; preferably about 0.5–20 mg/kg/day. Thus, for administration to a 70 kg person, the dosage range would most preferably be about 35 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical*

Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described in Example 19.

EXAMPLES

The following preparations and examples are given to enable those skilled in the art to more clearly understand and to practice the present invention. They should not be considered as limiting the scope of the invention, but merely as being illustrative and representative thereof.

Example 1

Synthesis of 3-(4-Fluorophenyl)-2-(pyridin-4-yl)-1H-pyrrolo[3,2-b]pyridine (following Scheme A)

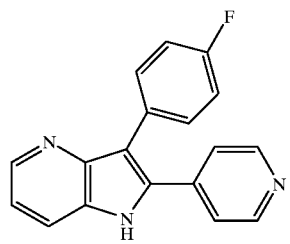

Step 1

Sodium metal (5.06 g, 210 mmol) was dissolved in absolute ethanol (150 ml) and then a solution of methyl isonicotinate (20.55 g, 150 mmol) and 4-fluorophenylacetonitrile (20.25 g, 150 mmol) in absolute ethanol (50 ml) was added in one portion. The reaction mixture was heated at reflux for 3 h and then cooled to room temperature. The reaction mixture was poured into ice water (300 ml) and the pH was adjusted to pH=3 with 10% hydrochloric acid. The yellow precipitate was filtered and dried in vacuo to give 24 g of cyano ketone. This material was suspended in 48% hydrobrormic acid (90 ml) and heated at reflux. After 8 h, the reaction mixture was cooled to room temperature and carefully poured into ice water (300 mnl). The pH was adjusted to pH=7–8 with ammonium hydroxide. The product was extracted into ethyl acetate and the combined organic layers were washed with brine, dried over MgSO$_4$ and concentration in vacuo to give 2-(4-fluorophenyl)-1-(pyridin-4-yl)ethanone (11.8 g) as a tan solid.

Step 2

To a solution of 2-(4-fluorophenyl)-1-(pyridin-1-yl) ethanone (5.20 g, 24 mmol) and 3-amino-2-chloropyridine (4.04 g, 31.4 mmol) in toluene (150 ml) was added p-toluenesulfonic acid monohydrate (457 mg. 2.4 mmol) and the reaction mixture was brought to reflux with Dean-Stark removal of the toluene/water azeotrope. After 24 h, toluene was removed in vacuo and the residue was resuspended in ethyl acetate. The precipitate was collected by vacuum filtration to give (2-chloropyridin-3-yl)-[2-(4-fluorophenyl)-1-(pyridin-4-yl)vinyl]amine (5.0 g) as a tan solid. The filtrate was concentrated in vacuo and purified by flash column chromatography (50%–80% ethyl acetate:hexanes gradient) to give additional 1.50 g of product.

Step 3

To a solution of (2-chloropyridin-3-yl)-[2-(4-fluorophenyl)-1-(pyridin-4-yl)vinyl]amine (6.0 g, 18.5 mmol) and DABCO® (6.2 g, 55 mmol) in dimethylformamide (75 ml) was added bis(triphenylphosphine)palladium (II) chloride (650 mg, 0.926 mmol) and the reaction mixture was heated at 120° C. under an argon atmosphere. After 4 h, dimethylformamide was removed in vacuo and the residue was heated in ethyl acetate/methanol mixture. The product was filtered off to give a green solid which was redissolved in boiling methanol/chloroform mixture and treated with charcoal. The solution was filtered through a pad of Celite and the filtrate was concentrated to give 3-(4-fluorophenyl)-2-(pyridin-4-yl)-1H-pyrrolo[3,2-b]pyridine as a pale yellow solid (5.27 g).

Example 2

Synthesis of 1-Ethyl-3-(4-fluorophenyl)-2-(pyridin-4-yl)-1H-pyrrolo[3,2-b]pyridine (following Scheme A)

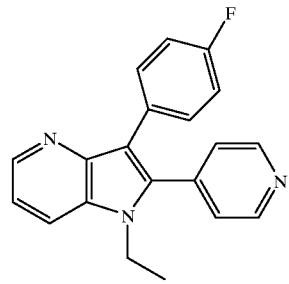

To a solution of 3-(4-fluorophenyl)-2-(pyridin-4-yl)-1H-pyrrolo[3,2-b]pyridine (100 mg, 0.346 mmol) [prepared as described in Example 1] in dimethylformamide (3 ml) was added sodium hydride (41 mg, 1.025 mmol, 60% in oil). After stirring at room temperature for 10 min., ethyl iodide (31 µl, 0.385 mmol) was added by syringe. After 2 h, dimethylformamide was removed in vacuo and the residue was redissolved in ethyl acetate (5 ml) and methanol (5 ml). The solution was washed with saturated sodium bicarbonate solution. The organic layer was separated, dried over MgSO$_4$ and concentration in vacuo to give a brown oil. Purification by flash column chromatography (50%–80% ethyl acetate:hexanes gradient) gave a yellow oil (60 mg) which was recrystallized from ethyl acetate:hexanes to give 1-ethyl-3-(4-fluorophenyl)-2-(pyridin-4-yl)-1H-pyrrolo[3, 2-b]pyridine as a white solid.

Example 3

Synthesis of 3-(4-Fluorophenyl)-2-(pyridin-4-yl)-1H-pyrrolo[3,2-c]pyridine (following Scheme C)

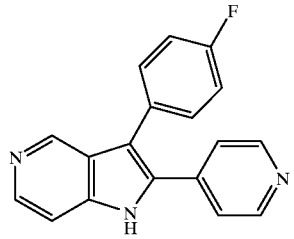

Step 1

To a solution of 4-pivaloylaminopyridine (7.0 g, 39 mmol) in tetrahydrofuran (100 ml) was added n-butyllithium (39.3 ml, 98 mmol, 2.5 M solution in tetrahydrofuran) at −78° C. under a $N_2$ atmosphere. The reaction mixture was stirred at 0° C. for 5 h, re-cooled to −78° C. and quenched with a solution of N-methoxy-N-methyl-4-fluorobenzamide (7.9 g, 43 mmol) in 100 ml tetrahydrofuran. The reaction mixture was warmed to room temperature and poured into water. The product was extracted into ethyl acetate. The organic layers were washed with brine, dried over sodium sulfate and evaporated to dryness. The residue was purified by flash chromatography (10% ethyl acetate/hexanes gradient) to afford N-[3-(4-fluorobenzoyl)pyridin-4-yl]-2,2-dimethylpropanamide (10 g).

Step 2

A solution of N-[3-(4-fluorobenzoyl)pyridin-4-yl]-2,2-dimethylpropanamide (2.85 g, 9.5 mmol) in 3 N aqueous HCl (15 ml) was warmed at reflux overnight. After cooling to room temperature, the reaction mixture was washed with ether, the aqueous layer was separated and neutralized with potassium carbonate. The product was extracted into ethyl acetate, dried over potassium carbonate/sodium carbonate and concentrated. The residue was purified by flash chromatography (5% methanol/methylene chloride gradient) to afford 4-amino-3-(4-fluorobenzoyl)pyridine (1.58 g).

Step 3

4-amino-3-(4-fluorobenzoyl)pyridine (1.5 g, 7.0 mmol) was suspended in methylene chloride (90 ml) and pyridine (2.24, 28 mmol). The reaction mixture was cooled to 0° C. and isonicotinoyl chloride (1.4 g, 7.6 mmol) was added. The reaction mixture was allowed to warm to room temperature, and stirring was continued for 4 h. Methylene chloride was added and the white precipitate was filtered and dried in vacuo to yield 3-(4-fluorobenzoyl)-4-(isonicotinoylamide)pyridine (1.7 g).

Step 4

A suspension of 3-(4-fluorobenzoyl)-4-(isonicotinoylamide)pyridine (300 mg, 0.75 mmol), titanium trichloride (6.3 ml, 6.3 mmol, 1.0 M solution in dichloromethanel tetrahydrofuran 2:1), magnesium (309 mg, 12.7 mmol) and pyridine (0.62 ml, 8.0 mmol) in ethylene glycol dimethyl ether (50 ml) was refluxed for 1 h. The reaction mixture was cooled to room temperature, diluted with ethyl acetate and a solution of 5% sodium bicarbonate was added. The reaction mixture was vigorously stirred overnight and then filtered through a pad of Celite. The organic layer was separated and concentrated in vacuo. Purification by flash chromatography (5% methano/methylene gradient) gave 3-(4-fluorophenyl)-2-(pyridin-4-yl)-1H-pyrrolo[3,2-c]pyridine as a solid (30 mg).

Example 4

Synthesis of 3-(4-Fluorophenyl)-1-hydroxy-2-(pyridin-4-yl)-1H-pyrrolo[3,2-b]pyridine (following Scheme D)

Step 1

To a solution of 2-(4-fluorophenyl)-1-(pyridin-4-yl) ethanone (4.0 g, 18.6 mmol) [prepared as described in Example 1 above] and 2-chloro-3-nitropyridine (6.50 g, 41.13 mmol) in dimethylformamide (50 ml) at 0° C. was added sodium hydride (1.65 g, 41 mmol, 60% in oil) under an argon atmosphere. The reaction mixture was warmed to room temperature and stirred for an hour. The reaction mixture was quenched with water and the product was extracted into ethyl acetate. The combined organic extracts were washed with brine, dried over $MgSO_4$ and concentrated in vacuo to give a dark brown oil. Purification by flash column chromatography (10% to 50% ethyl acetate/hexanes gradient) gave 2-(4-fluorophenyl)-2-(3-nitropyridin-2-yl)-1-(pyridinyl)ethanone as a brown oil (4.08 g).

Step 2

A solution of gave 2-(4-fluorophenyl)-2-(3-nitropyridin-2-yl)-1-(pyridin-4-yl)ethanone (2.0 g, 5.93 mmol) and pyridine (0.52 g, 6.53 mmol) in dichloromethane (30 ml) was added to a cold solution of trifluoromethanesulfonic anhydride (1.1 ml, 6.53 mmol) in dichloromethane (7 ml) at 0° C. After 1 h, the reaction mixture was poured into water (50 mnl) and the product was extracted into dichloromethane. The combined organic extracts were washed with saturated sodium bicarbonate solution and brine and dried over $MgSO_4$. Concentration in vacuo gave a brown oil which was purified by flash column chromatography (50%–60% ethyl acetate/hexanes gradient) to give the trifluoromethanesulfonic acid 2-(4-fluorophenyl)-2-(3-nitropyridin-2-yl)-1-(pyridin-4-yl)vinyl ester as a light tan oil (1.56 g).

Step3

To a solution of trifluoromethanesulfonic acid 2-(4-fluorophenyl)-2-(3-nitropyridin-2-yl)-1-(pyridin-4-yl)vinyl ester (1.5 g, 3.20 mmol) in ethyl acetate (50 ml) was added stannous chloride dihydrate (2.89 g, 12.8 mmol) and the reaction mixture was warmed to 50° C. After 1 h, the warm solution was treated with saturated sodium bicarbonate solution (10 ml) and filtered through Celite. The filtrate was washed with brine, dried over anhydrous sodium sulfate and concentrated in vacuO. Purification by flash column chromatography ($CH_2Cl_2$–95% $CH_2Cl_2$/MeOH gradient) gave 3-(4-fluorophenyl)-1-hydroxy-2-(pyridin-4-yl)-1H-pyrrolo[3,2-b]pyridine as a tan solid (700 mg).

Example 5

Synthesis of 3-(4-Fluorophenyl)-1-methoxy-2-(pyridin-4-yl)-1H-pyrrolo[3,2-b]pyridine (following Scheme D)

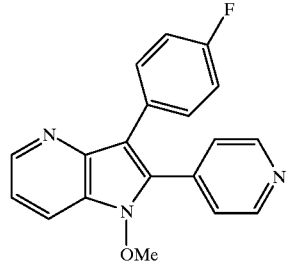

A solution of 3-(4-fluorophenyl)-1-hydroxy-2-(pyridin-4-yl)-1H-pyrrolo[3,2-b]pyridine (0.38 g, 1.25 mmol) in chloroform (8 ml) and methanol (2 ml) was added to a solution of diazomethane at 0° C. The reaction was warmed to room temperature and stirred overnight. The solvent was removed in vacuo and the residue was purified by flash column chromatography (50%–100% ethyl acetate/hexanes gradient) to 3-(4-fluorophenyl)-1-methoxy-2-(pyridin-4-yl)-1H-pyrrolo[3,2-b]pyridine as an off white solid (210 mg).

Example 6

Synthesis of 3-(4-Fluorophenyl)-1-[2-(morpholin-4-yl)ethoxy]-2-(pyridin-4-yl)-1H-pyrrolo[3,2-b]pyridine (following Scheme D)

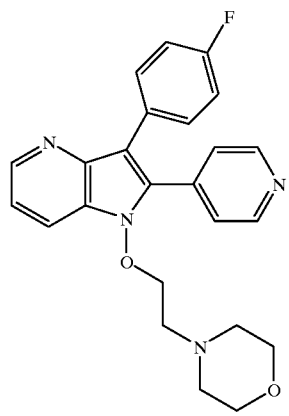

To a solution of 3-(4-fluorophenyl)-1-hydroxy-2-(pyridin-4-yl)-1H-pyrrolo[3,2-b]pyridine (0.20 g, 0.65 mmol) and 2-chloroethylmorpholine hydrochloride (0.24 g, 6.56 mmol) in dimethylformamide (5 ml) was added sodium hydride (100 mg, 60% in oil). The reaction mixture was stirred overnight and quenched with 10% HCl (2 ml). The pH was adjusted to pH=8–9 by the addition of saturated sodium bicarbonate solution and the product was extracted into ethyl acetate. The combined extracts were dried over anhydrous MgSO4 and concentrated in vacuo to give an oil. Purified by flash column chromatography (50%–80% ethyl acetate/hexanes, followed by 95/5% methylene chloride/methanol gradient) gave 3-(4-fluorophenyl)-1-[2-(morpholin-4-yl)ethoxy]-2-(pyridin-4-yl)-1H-pyrrolo[3,2-b]pyridine (180 mg) which recrystallized from hexanes/ethyl acetate to give a white solid.

Example 7

Synthesis of 3-(4-Fluorophenyl)-1-[2-(piperidin-1-yl)ethoxy]-2-(pyridin-4-yl)-1H-pyrrolo[3,2-b]pyridine (following Scheme D)

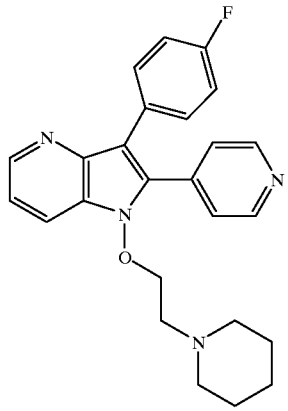

To a solution of 3-(4-fluorophenyl)-1-hydroxy-2-(pyridin-4-yl)-1H-pyrrolo[3,2-b]pyridine (0.20 g, 0.65 mmol) and 2-chloroethylpiperidine hydrochloride (0.24 g, 1.31 mmol) in dimethylformamide (5 ml) was added sodium hydride (100 mg, 6.56 mmol, 60% in oil). The reaction mixture was stirred overnight and quenched with water (2 ml). The pH was adjusted to pH=11–12 by the addition of saturated sodium carbonate solution and the product was extracted into ethyl acetate. The combined extracts were dried over anhydrous MgSO4 and concentrated in vacuo to give an oil. Purified by flash column chromatography (50%–80% ethyl acetate/hexanes, followed by 95/5% methylene chloride/methanol gradient) gave 3-(4-fluorophenyl)-1-[2-(piperidin-1-yl)ethoxy]-2-(pyridin-4-yl)-1H-pyrrolo[3,2-b]pyridine as a yellow solid (182 mg).

Proceeding as described above but substituting 2-chloroethylpiperidine hydrochloride with 2-chloroethylpyrrolidine hydrochloride gave 3-(4-fluorophenyl)-2-(pyridin-4-yl)-1-[2-(pyrrolidin-1-yl)ethoxy)-1H-pyrrolo[3,2-b]pyridine.

Example 8

Synthesis of 7-(4-Fluorophenyl)-6-(pyridin-4-yl)-5H-pyrrolo[2,3-b]pyrazine (following Scheme I)

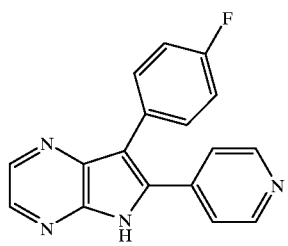

Step 1

To a solution of chloropyrazine (11.5 g, 0.1 mmol) in absolute ethanol (50 ml) was added anhydrous hydrazine (16 ml, 0.5 mmol) and the reaction mixture was refluxed for 3 h. The organics were removed in vacuo and the residue was extracted with benzene to give hydrazinopyrazine (4.2 g).

Step 2

To a suspension of hydrazinopyrazine (2.9 g, 26 mmol) in benzene (120 ml) was added 2-(4-fluorophenyl)-1-(pyridin-4-yl)ethanone (5.6 g, 26 mmol) and p-toluenesulfonic acid (0.30 g). The reaction mixture was refluxed with azeotropic removal of water. After 2.5 h, the reaction mixture was concentrated in vacuo to give pyrazinylhydrazone (8.8 g) which was used in the next step without further purification.

Step 3

The pyrazinylhydrazone (8.8 g) was suspended in diethylene glycol (75 ml) and the reaction mixture was heated at reflux. After 1.5 h, the reaction mixture was cooled, and poured in water. The product was extracted into diethyl ether and the ethereal layer was washed with brine and concentrated in vacuo. The crude product was recrystallized from methanol to give 7-(4-fluorophenyl)-6-(pyridin-4-yl)-5H-pyrrolo[2,3-b]pyrazine as a solid (1.1 g).

Example 9

Synthesis of 1-(3-Chloropropyl)-7-(4-fluorophenyl)-6-(pyridin-4-yl)-5H-pyrrolo[2,3-b]pyrazine

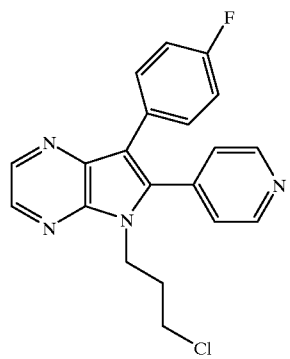

To a suspension of sodium hydride (1.03 g, 25.8 mmol, 60% in mineral oil) in dry tetrahydrofuran (20 ml) was slowly added 7-(4-fluorophenyl)-6-(pyridin-4-yl)-5H-pyrrolo[2,3-b]pyrazine (0.75 g, 2.58 mmol) followed by 1-bromo-3-chloropropane (4.05 g, 25.8 mmol). The reaction mixture was heated at 65° C. for 72 h. Water was added slowly to quench the excess sodium hydride and the organics were removed in vacuo. Water was added to the residue and the aqueous layer was extracted with ethyl acetate. The organic phase was washed with brine, dried over magnesium sulfate, filtered and concentrated in vacuo. The crude product was purified by flash chromatography on silica gel, elating with ethyl acetate, to give 1-(3-chloropropyl)-7-(4-fluorophenyl)-6-(pyridin-4-yl)-5H-pyrrolo[2,3-b]pyrazineas a solid (0.375 g).

Example 10

Synthesis of 7-(4Fluorophenyl)-1-[3-(4-methyimidazol-1-yl)propyl]-6-(pyridin-4-yl)-5H-pyrrolo[2,3-b]pyrazine

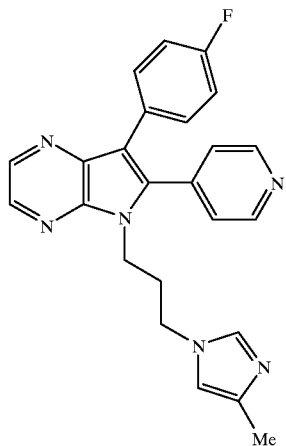

To a solution of 1-(3-chloropropyl)-3-(4-fluorophenyl)-2-(pyrindin4-yl)-5H-pyrrolo[2,3-b]pyrazine (0.050 g, 0.14 mmol) in dimethylformamide was added 4-methylimidazole (0.046 g, 0.4 mmol) and diisopropylethyl amine (0.12 ml, 0.7 mmol). The solution was heated at 65° C. for 16 h. The compound was purified by reverse phase chromatography to yield pure 3-(4-fluorophenyl-1-[3-(4-methyimidazol-1-yl)propyl]-6-(pyridin-4-yl)-5H-pyrrolo[2,3-b]pyrazine(0.039 g).

Example 11

Synthesis of 6-(2-Bromopyridin-4-yl)-7-(4-fluorophenyl)-5H-pyrrolo[2,3-b]pyrazine

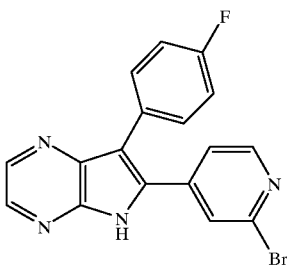

Step 1

2-Chloropyridine-4-carboxylic acid (15.5 g, 98 mmol) was suspended in methanol (175 ml) and anhydrous hydrogen chloride gas was slowly bubbled through the reaction mixture while cooling in a methanol/water (20/80) dry ice bath. Bubbling was continued for 40 min. during which time the suspension cleared to a partial solution. Ice bath was removed and the reaction mixture was heated to reflux under anhydrous conditions for 30 min. to give a clear yellow solution. The solution was cooled in an ice bath and saturated sodium bicarbonate was slowly added with stirring till the pH was neutral. The organics were removed in vacuo and the product was extracted into ethyl acetate. The ethyl acetate layer was dried over sodium sulfate, filtered, and concentrated in vacuo to yield 2-chloropyridine-4-carboxylic acid methyl ester as a brown liquid.

Step 2

4-Fluorophenylacetonitrile (11.13 g, 82 mmol) was dissolved in absolute ethanol (100 ml) and sodium ethoxide (21wt % in EtOH) (46 ml, 123 mmol) was added in one portion. The resulting brown solution was stirred for 10 min. at room temperature. A solution of 2-chloropyridine-4-carboxylic acid methyl ester (14.1 g, 82 mmol) in absolute ethanol (100 ml) was then added to the reaction over 3–5 min. The reaction mixture was then refluxed for 2 h during which time the color turned to dark brown. The reaction mixture was concentrated in vacuo and water (100 ml) was added to the resulting residue. The pH of the reaction mixture was adjusted to 3 using 10% hydrochloric acid. The product was extracted with ethyl acetate and the combined ethyl acetate extracts were dried over sodium sulfate, filtered and concentrated in vacuo to yield 1-(2-chloropyridin-4-yl)-2-cyano-2-(4-fluorophenyl)ethanone as a dark brown solid which was used without further purification (22.0 g).

Step 3

To 1-(2-chloropyridin-4-yl)-2-cyano-2-(4-fluorophenyl)ethanone (22.0 g, 80 mmol) was added 48% hydrobromic acid (75 ml) and the reaction mixture was heated at reflux in an oil bath at 135° C. After 4 h, the reaction mixture was allowed to cool to room temperature and then further cooled in an ice bath. Saturated sodium bicarbonate (100 ml) was carefully added, followed by solid portions of sodium bicarbonate until the pH of the reaction mixture was neutral. The reaction mixture was then extracted with ethyl acetate and the ethyl acetate layer was dried over sodium sulfate, filtered and concentrated to a brown semi-solid (2.8 g). The crude product was purified by flash chromatography on silica gel, eluting with 1:1 mixture of ethyl acetate/hexanes to give 1-(2-bromopyridin-4-yl)-2-(4-fluorophenyl)ethanone (1.9 g).

Step 4

Hydrazinopyrazine (0.71 g, 6.4 mmol) and 1-(2-bromopyridin-4-yl)-2-(4-fluorophenyl)ethanone (1.9 g, 6.4 mmol) were suspended in benzene (30 ml) and p-toluenesulfonic acid monohydrate (0.02 g) was added. The reaction mixture was then refluxed with azeotropic removal of water via Dean Stark trap. The benzene was then removed in vacuo to give the crude N-[1-(3-bromopyridin-4-yl)-2-(4-fluorophenyl)ethylidene]-N'-pyrazin-2-ylhydrazine as a yellow semi-solid which was used without further purification (2.4 g).

Step 5

N-[1-(3-Bromopyridin-4-yl)-2-(4-fluorophenyl)ethylidene]-N'-pyrazin-2-ylhydrazine(2.4 g, 6.2 mmol) was suspended in di(ethylene glycol) (30 ml) and heated in an oil bath at 250° C. After 1 h, the reaction mixture was allowed to cool and then poured into a separatory funnel containing water (50 ml). The reaction mixture was then extracted with diethyl ether. The ether extracts were combined, dried over sodium sulfate, filtered, and concentrated in vacuo to yield the crude brown solid (2.0 g). The solid was recrystallized from ethyl acetate/methanol 1:1 (25 ml) mixture to yield the 6(2-bromopyridin-4-yl)-7-(4-fluorophenyl)-5H-pyrrolo[2,3-b]pyrazine as a tan solid (0.650 g).

Example 12

Synthesis of the 7-(4-Fluorophenyl)-6-[2-(3-hydroxypropylamino)pyridin-4-yl]-5H -pyrolo[2,3-b]pyrazine hydrochloride salt

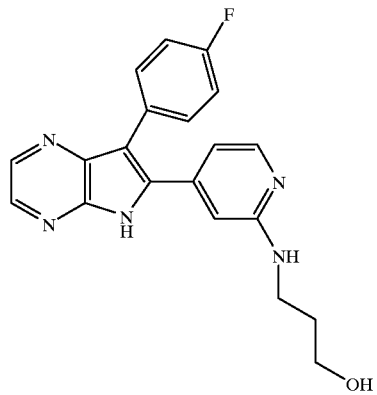

Step 1

6-(2-Bromopyridin-4-yl)-7-(4-fluorophenyl)-5H-pyrrolo[2,3-b]pyrazine(0.05 g, 0.135 mmol) was dissolved in 3-amino-1-propanol (0.5 ml, 6.5 mmol) and the reaction mixture was heated in a sealed vial at 110° C. After 20 h, the reaction mixture was purified by reverse phase chromatography to yield the 7-(4-fluorophenyl)-6-[2-(3-hydroxypropylamino)pyridin-4-yl]-5H-pyrrolo[2,3-b]pyrazine trifluoroacetate salt as a yellow oil (0.018 g).

Step 2

7-(4-Fluorophenyl)-6-[2-(3-hydroxypropylamino)pyridin-4-yl]-5H-pyrrolo[2,3-b]pyrazine trifluoroacetate salt (0.018 g, 0.05 mmol) was treated with HCl/diethyl ether (1.0 ml of a 1.0 M solution) to give a solid . The ethereal layer was decanted off and the resulting solid was washed twice with ether. Excess ether was carefully blown off with nitrogen gas and the resulting yellow solid was dried in vacuo to 7-(4-fluorophenyl)-6-[2-(3-hydroxypropylamino)pyridin-4-yl]-5H-pyrrolo[2,3-b]pyrazine hydrochloride salt (0.0 1 9 g).

Example 13

Synthesis of the 3-(4-Fluorophenyl)-2-(pyridin-4-yl)-furo[3,2-b]pyridine (following Scheme E)

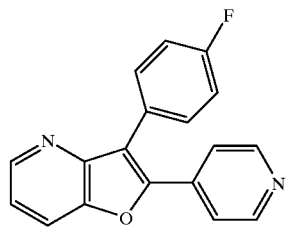

Step 1

3-Hydroxypicolinic acid (12.5 g, 900 mmol) was suspended in a mixture of ethanol (300 ml) and benzene (100 ml). Sulfuric acid (5 ml) was added and the reaction mixture was heated at reflux with azeotropic removal of water via Dean Stark trap. After the reaction was complete, the organics were removed in vacuo. The residue was dissolved in water, basified with sodium carbonate and extracted with ethyl acetate. The ethyl acetate layer was dried over magnesium sulfate, concentrated in vacuo to give ethyl 3-hydroxypicolinate (15 g).

Step 2

A mixture of ethyl 3-hydroxypicolinate (15 g, 900 mmol), tributylsilyl chloride (16.23 g, 110 mmol), imidazole (8.0 g, 120 mmol) in methylene chloride was stirred overnight under a nitrogen atmosphere. Water was added and the methylene chloride layer was separated and concentrated in vacuo. Purification on a silica gel column using ethyl acetate-hexane (1:4) as the eluant gave ethyl 3-(tributylsilyloxy)picolinate as a solid (20 g).

Step 3

A solution of ethyl 3-(tributylsilyloxy)picolinate (19 g, 35 mmol) in tetrahydrofuran (100 ml) was cooled to 0° C. and 4-fluorophenylmagnesium chloride (52 ml, 1.0 M in tetrahydrofuran) was added dropwise. After 30 min., the reaction mixture was quenched with water and the product was extracted with ethyl acetate. The organic layer was dried over sodium sulfate and concentrated in vacuo. Purification on a silica gel column using ethyl acetate-hexane (2:98) as the eluant gave 2-(4-fluorobenzoyl)-3-(tributylsilyloxy)pyridine (3.75 g).

Step 4

A solution of 2-(4-fluorobenzoyl)-3-(tributylsilyloxy)pyridne (3.75 g, 11.3 mmol) in tetrahydrofuran (17 ml) was cooled to 0° C. and tetrabutylammonium fluoride (17 ml, 1.0 M in tetrahydrofuran) was added. After 2 h, the reaction mixture was diluted with ethyl acetate. The organic layer was separated, washed with sodium bicarbonate and brine, and dried over sodium sulfate. The organics were removed in vacuo and the residue was purified on a silica gel column using ethyl acetate-hexane (2:8) as the eluant to give 2-(4-fluorobenzoyl)-3-hydroxypyridine (2.2 g).

Step 5

A mixture of give 2-(4-fluorobenzoyl)-3-hydroxypyridine (2.2 g, 11.3 mmol), ethyl bromoacetate (1.6 ml, 14.15 mmol) and potassium carbonate (4.34 g, 31.4 mmol) in acetone (40 ml) was heated at reflux. After 3 h, the reaction was cooled to room temperature, filtered and concentrated in vacuo to give ethyl 2-[2-(4-fluorobenzoyl)pyridin-3-yloxy]acetate (3.5 g) which was used in the next step without further purification.

Step 6

Sodium ethoxide (1.51 g. 22.6 mmol) was suspended in toluene (25 ml) and ethyl 2-[2-(4-fluorobenzoyl)pyridin-3-yloxy]acetate (3.5 g, 11.5 mmol) was added. The reaction was heated at reflux under an argon atmosphere. After 12 h, the reaction mixture was cooled to room temperature and the product was extracted into water. The aqueous layer was acidified with hydrochloric acid to give 2-carboxy-3-(4-fluorophenyl)-furc[3,2-b]pyridine as a solid (1.8 g).

Step 7

A mixture of 2-carboxy-3-(4-fluorophenyl)-furo[3,2-b]pyridine (1.8 g, 7 mmol), copper metal (0.56 g, 8.81 mmol) in quinoline (10 ml) was heated at reflux. After 45 min., the reaction was cooled to room temperature and the product was extracted into water. The aqueous layer was acidified with hydrochloric acid and acetic acid. The product was filtered and dissolved in ether. The ether layer was dried over sodium sulfate and concentrated in vacua. Purification by flash chromatography using ethyl acetate-hexanes (1:9) as the eluant gave 3-(4-fluorophenyl)-furo[3,2-b]pyridine as a solid (0.85 g).

Step 8

A solution of 3-(4-fluorophenyl)-furo[3,2-b]pyridine (0.40 g, 1.84 mmol) and N,N,N',N'-tetramethylethylenediamnine (0.33 g, 7.2 mmol) in tetrabydrofuran (15 ml) was cooled to −78° C. n-Butyllithium (1.1 ml, 2.5 M in hexanes, 2.7 mmol) was added and the reaction mixture was allowed to warm to room temperature. After 1.5 h, the reaction mixture was re-cooled to −78° C. and n-tributyltin chloride (0.5 ml, 1.84 mmol) was added. The reaction was allowed to warm to room temperature and then quenched with aqueous ammonium chloride. The product was extracted into ether and the ether layer was dried over sodium sulfate and concentrated in vacuo. Purification by flash chromatography using hexanes, followed by ethyl acetate-hexanes (5:95) as the eluant gave 3-(4-fluorophenyl)-2-(n-tributyltin)-furo[3,2-b]pyridine (0.72 g).

Step 9

A mixture of 3-(4-fluorophenyl)-2-(n-tributyltin)-furo[3,2-b]pyridine (0.72 g, 1.4 mmol), tetrakis(triphenylphosphine)palladium (II) (0.165 g, 0.14 mmol) and 4-bromopyridine [prepared from 4-bromopyridine hydrochloride (1.4 g, 7.15 mmol)] in xylenes (20 ml) was heated at reflux under an argon atmosphere. After 12 h, the reaction mixture was cooled to room temperature and purified by flash chromatography using hexanes, followed by ethyl acetate-hexanes (5: 95) as the eluant to give 3-(4-fluorophenyl)-2-(pyridin-4-yl)-furo[3,2-b]pyridine. Recrystallized from ethyl acetate-hexanes mixture to give pure product (0.15 g).

Example 14

Synthesis of the 3-(4-Fluorophenyl)-7-methylthio-2-(pyridin-4-yl)-pyrrolo[3,2-b]pyridine

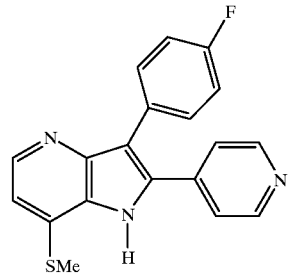

Step 1

2,2,6,6-Tetramethylpiperidine (1.76 ml, 10.40 mmol) was dissolved in tetrahydrofuran (39 ml) and placed under an atmosphere of nitrogen. The solution was cooled to −78° C. and n-butyllithium (3.96 ml, 9.91 mmol, 2.5 M solution of in hexanes) was added at such a rate that the internal temperature did not exceed −70° C. The reaction mixture was warmed to −10° C. for 30 min., then re-cooled to −78° C. A solution of 1-tert-butoxycarbonyl-3-(4-fluorophenyl)-2-(pyridin-4-yl)-pyrrolo[3,2-b]pyridine (0.965g, 2.47 mmol) in tetrahydrofuran (32 ml) was cooled to −78° C. and then added via cannula at such a rate that the internal temperature did not exceed −70+ C. After 1 h, dimethyldisulfide (0.29 ml, 3.22 mmol) was added and the resulting solution was stirred for an additional 1 h at −78° C. The reaction mixture was quenched with saturated ammonium chloride solution and the product was extracted into ethyl acetate. The organic layer was washed with brine, dried over anhydrous sodium sulfate, and concentrated in vacuo. The crude residue was purified by flash chromatography using 20% acetone/hexanes as the eluant to give 1-tert-butoxycarbonyl-3-(4-fluorophenyl)-7-methylthio-2-(pyridin-4-yl)-pyrrolo[3,2-b]pyridine. MS: 435 (M).

Step 2

1-Tert-butoxycarbonyl-3-(4-fluorophenyl)-7-methylthio-2-(pyridin-4-yl)-pyrrolo[3,2-b]pyridine (29 mg, 0.064 mmol was dissolved in dimethylsulfoxide (1 ml) and the solution was heated to 73° C. After 20 h, the solution was cooled and partitioned between ethyl acetate and water. The organic layer was separated and washed with brine, dried over anhydrous magnesium sulfate, and concentrated in vacuo to give 3-(4-fluorophenyl)-7-methylthio-2-(pyridin-4-yl)-pyrrolo[3,2-b]pyridine.

Example 15

Synthesis of the 2-(2-Chloropyrimidin-4-yl)-3-(4-fluorophenyl)-furo[3,2-b]pyridine (following Scheme E)

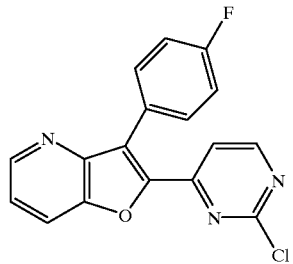

A mixture of 3-(4-fluorophenyl)-2-(n-tributyltin)-furo[3,2-b]pyridine (2.38 g, 4.73 mmol), [prepared as described in Example 13 above], bis-dichlorotriphenylphosphine-palladium (0.33 g, 0.47 mmol) and 2,4-dichloropyrimidine (3.52 g, 23.65 mmol)] in dimethylformamide (20 ml) was heated at 100° C. under an argon atmosphere. After 12 h, the reaction mixture was cooled to room temperature, quenched with water and the product was extracted into ethyl acetate. The organic layer was dried over sodium sulfate, concentrated in vacuo and the residue was purified by flash chromatography using 80% ethyl acetate-hexanes as the eluant to give 2-(2-chloropyrimidin-4-yl)-3-(4-fluorophenyl)-furo[3,2-b]pyridine.

Example 16

Synthesis of the 2-(2-Aminopyrimidin-4-yl)3-(4-fluorophenyl)-furo[3,2-b]pyridine (following Scheme E)

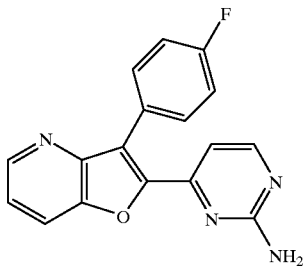

2-(2-Chloropyrimidin-4-yl)-3-(4-fluorophenyl)-furo[3,2-b]pyridine (0.15 g) was dissolved in ethanol (10 ml) and ammonia was bubbled through the solution until it was saturated. The reaction mixture was heated in a sealed tube at 100° C. After 12 h, the solvent was removed in vacuo and the residue was purified by flash chromatography using 50% ethyl acetate-hexanes as the eluant to give 2-(2-aminopyrimidin-4-yl)-3-(4-fluorophenyl)-furo[3,2-b]pyridine (0.70 g) as a solid.

Example 17

Synthesis of 1-(4-Fluorophenyl)-4-methyl-2-(pyridin-4-yl)-1H-pyrrolo[2,3-b]pyridine

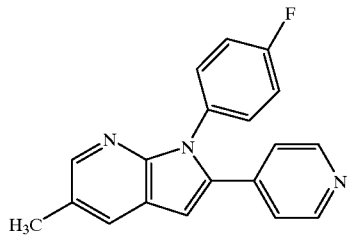

Step 1

To a solution of 2-amino-3-bromo-5-methylpyridine (5.48 g, 29 mmol) and 4-acetylpyridine (2.67 ml, 24 mmol) in toluene (200 ml) was added p-toluenesulfonic acid (0.1 g) and the reaction mixture was refluxed under argon atmosphere. After 4 days, the reaction mixture was cooled to room temperature and the organics were removed in vacuo. The residue was purified by flash chromatography using 50% ethyl acetate-hexanes, followed by ethyl acetate as the eluant to (3-bromo-5-methylpyridin-2-yl)-(1-pyridin-4-ylethylidene)amine (4.29 g) as an oil.

Step 2

To a solution of (3-bromo-5-methylpyridin-2-yl)-(1-pyridin-4-ylethylidene)amine (4.25 g, 14.65 mmol) in dimethylformamide (75 ml) was added DABCO® (4.93 g, 43.96 mmol) and], bis-dichlorotriphenylphosphine palladium (0.52 g, 0.73 mmol). The reaction mixture was heated at 120° C. under argon atmosphere. After 1.5 days, the reaction mixture was cooled into room temperature and poured into 10% hydrochloric acid (100 ml). The solution was filtered through Celite® and the filtrate was neutralized to pH 7 with 10% sodium hydroxide and the solid was filtered off to give 4-methyl-2-(pyridin-4-yl)-1H-pyrrolo[2,3-b]pyridine (1.57 g) as a brown solid.

Step 3

To a solution of 4-methyl-2-(pyridin-4-yl)-1H-pyrrolo[2,3-b]pyridine (0.3 g, 1.43 inmol) in N-methylpyrrolidone (5 ml) was added 4-bromofluorobenzene (0.57 ml, 5.2 mmol), copper bromide (0.205 g, 1.43 mmol) and sodium carbonate (0.15 g, 1.43 mmol) and the reaction mixture was heated to 180° C. under argon. After 24 h, the reaction mixture was cooled and poured into 10% hydrochloric acid (50 ml). The solution was filtered through Celite® and the filtrate was neutralized to pH 7 with 10% sodium hydroxide. The solid was filtered off, dissolved in 80% methanol:methylene chloride and purified by preparatory thin layer chromatography to give 1-(4-fluorophenyl)-4-methyl-2-(pyridin-4-yl)-1H-pyrrolo[2,3-b]pyridine (0.03 g) as a tan solid.

Example 18

Synthesis of the 6-[2-(Acetylamino)pyridin-4-yl]-7-(4-fluorophenyl)-5H-pyrrolo[2,3-b]pyrazine hydrochloride salt

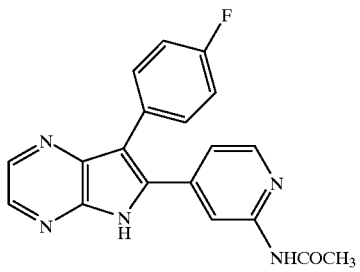

Step 1

To a solution of magnesium turnings (7.3 g, 300 mmol) in anhydrous ether (115 ml) was added a few crystals of iodine. A few drops of 4-fluorobenzyl chloride was added dropwise and the solution was heated to initiate the reaction. Once the reaction had initiated, the rest of 4-fluorobenzyl chloride (43 g, 300 mmol) was added at a rate that maintained a gentle reflux. After the addition was complete, the reaction was stirred for 1 h and was used in the next step.

Step 2

Sodium hydride (8.6 g, 220 mmol, 60% dispersion in mineral oil) was washed twice with hexane (50 ml) and suspended in tetrahydrofuran (400 ml). 2-Chloroisonicotinic acid (28 g, 180 mmol) was slowly added and the resulting slurry was heated at reflux. After 2 h, the reaction was cooled in an ice-bath and 4-fluorobenzylmagnesium chloride (100 ml, 200 mmol) was added. After stirring overnight, the reaction was quenched with 4 M ammonium chloride solution (100 ml). Water (100 ml) was added and the product was extracted into methylene chloride. The organic layer was washed with sat. sodium bicarbonate solution, dried over magnesium sulfate, filtered and concentrated in vacuo. The crude oil was purified by flash chromatography using 25% ethyl acetate-hexanes as the eluant to 1-(2-chloropyridin-4-yl)-2-(4-fluorophenyl)ethanone (14 g).

Step 3

Hydrazinopyrazine (6.2 g, 57 mmol) and 1-(2-chloropyridin-4-yl)-2-(4-fluorophenyl)ethanone (14 g, 57 mmol) were suspended in benzene (250 ml) and p-toluenesulfonic acid monohydrate (0.68 g) was added. The reaction mixture was then refluxed with azeotropic removal of water via Dean Stark trap. After 2 h, the benzene was removed in vacuo and di-ethylene glycol was added. The reaction mixture was heated at reflux. After 2 h, the reaction mixture was poured into ether with vigorous stirring. Water was added and the product was extracted into ether. The organic layer was dried over magnesium sulfate, filtered and concentrated in vacuo. Methanol was added and the solid was filtered off to give 6-(2-chloropyridin-4-yl)-7-(4-fluorophenyl)-5H-pyrrolo[2,3-b]pyrazine (4.9 g) as a solid.

Step 4

6-(2-Chloropyridin-4-yl)-7-(4-fluorophenyl)-5H-pyrrolo[2,3-b]pyrazine (0.5 g, 1.5 mmol) was dissolved in hot dimethylsulfoxide (3 ml) in a glass pressure tube and allowed to cool to room temperature. Ammonium hydroxide (3 ml) and copper sulfate pentahydrate (0.77 g, 3.0 mmol) were added and the reaction vessel was sealed with O-ring screw cap. The reaction mixture was heated for 72 h in a sand bath at 150° C. The reaction mixture was poured into ethyl acetate (200 ml) and water (100 ml) and the product was extracted into ethyl acetate. The organic layer was dried over sodium sulfate, filtered and concentrated in vacuo. The crude product was purified by reverse phase HPLC to give 6-(2-aminopyridin-4-yl)-7-(4-fluorophenyl)-5H-pyrrolo[2,3-b]pyrazine trifluoroacetate salt (0.1 g) as a yellow solid.

Step 5

6-(2-Aminopyridin-4-yl)-7-(4-fluorophenyl)-5H-pyrrolo[2,3-b]pyrazine trifluoroacetate salt (0.085 g, 0.28 mmol) was dissolved in tetrahydrofuran and pyridine (0.22 g, 2.8 mmol) was added. Acetyl chloride (0.033 g, 0.42 mmol) in tetrahydrofuran (1 ml) was added and the resulting mixture was stirred at room temperature. After 1 h, the reaction mixture was diluted with methanol (2 ml) and the product was isolated by reverse phase HPLC to give 6-(2-acetylaminopyridin-4-yl)-7-(4-fluorophenyl)-5H-pyrrolo[2,3-b]pyrazine trifluoroacetate salt (0.1 g) as a yellow solid. The product was converted to the hydrochloride salt by suspending the product in ether and adding 1.0M solution of HCl in ether (2 ml) to give a solid which was filtered off to give 6-(2-acetylaminopyridin-4-yl)-7-(4-fluorophenyl)-5H-pyrrolo[2,3-b]pyrazine hydrochloride salt (0.0.44 g) as a yellow solid.

Example 19

The following are representative pharmaceutical formulations containing a compound of Formula (I).

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |

-continued

| Ingredient | Amount |
| --- | --- |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 1.2 g |
| sodium acetate buffer solution, 0.4 M | 2.0 ml |
| HCl (1 N) or NaOH (1 N) | q.s. to suitable pH |
| water (distilled, sterile) | q.s.to 20 ml |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| compound of the invention | 500 mg |
| --- | --- |
| Witepsol ® H-15 | balance |

Example 20

Inhibition of p38 (MAP) Kinase . . . In Vitro Assay

The p-38 MAP kinase inhibitory activity of compounds of this invention in vitro was determined by measuring the transfer of the Tphosphate from $\gamma$-$^{33}$P-ATP by p-38 kinase to Myelin Basic Protein (MBP), using the a minor modification of the method described in Ahn, N. G.; et al. *J. of Biol. Chem.* Vol. 266(7), 4220–4227, (1991)

The phosphorylated form of the recombinant p38 MAP kinase was expressed with SEK-1 and MEKK in *E. Coli* (see, Khokhlatchev, A. et al. *J. of Biol. Chem.* Vol. 272(17), 11057–11062, (1997) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added and the samples were incubated for 10 min. at 30° C. The kinase reaction was initiated by the addition of a substrate cocktail containing MBP and $\gamma$-$^{33}$P-ATP. After incubating for an additional 20 min. at 30° C., the reaction was terminated by adding 0.75% phosphoric acid. The phosphorylated MBP was then separated from the residual $\gamma$-$^{33}$P-ATP using a phosphocellulose membrane (Millipore, Bedfrod, Mass.) and quantitated using a scintillation counter (Packard, Meriden, Conn.).

The p-38 inhibitory activities (expressed as $IC_{50}$, the concentration causing 50% inhibition of the p-38 enzyme being assayed) of some compounds of the invention is:

| CPD # | $IC_{50}$, nM | CPD # | $IC_{50}$, nM |
| --- | --- | --- | --- |
| 2 | 68 | 106 | 120 |
| 3 | 221 | 108 | 747 |
| 5 | 246 | 112 | 34.4 |
| 101 | 85.5 | | |

Example 21

Inhibition of LPS-Induced TNF-α Production in THP1 Cells . . . In Vitro Assay

The ability of the compounds of this invention to inhibit the TNF-α release was determined using a minor modification of the methods described in described in Blifeld, C. et al. *Transplantation*, Vol. 51(2), 498–503, (1991).

(a) Induction of TNF Biosynthesis:

THP-1 cells were suspended in culture medium [RPMI (Gibco-BRL, Gailthersburg, Md.) containing 15% fetal bovine serun, 0.02 mM 2-mercaptoethanol], at a concentration of $2.5 \times 10^6$ cells/ml and then plated in 96 well plate (0.2 ml aliquots in each well). Test compounds were dissolved DMSO and then diluted with the culture medium such that the final DMSO concentration was 5%. 20 μl aliquots of test solution or only medium with DMSO (control) were added to each well. The cells were incubated for 30 min., at 37° C. LPS (Sigma, St. Louis, Mo.) was added to the wells at a final concentration of 0.5 μg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNFα antibodies (2TNF-H22 and 2TNF-H34) described in Reimund, J. M., et al. *GUT.* Vol. 39(5), 684–689 (1996).

Polystyrene 96-well plates were coated with 50 μl per well of antibody 2TNF-H22 in PBS (10 μg/ml) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/ml followed by 6 half log serial dilution's.

25 μl aliquots of the above culture supernatants or TNF standards or only medium (control) were mixed with 25 μl aliquots of biotinylated monoclonal antibody 2TNF-H34 (2 μg/ml in PBS containing 0.1% BSA) and then added to each well. The samples were incubated for 2 h at room temperature with gentle shaking and then washed 3 times with 0.1% ATP BSA in PBS. 50 μl of peroxidase-streptavidin (Zymed, S. San Francisco, Calif.) solution containing 0.416 μg/ml of peroxidase-streptavidin and 0.1% BSA in PBS was added to each well. The samples were incubated for an additional 1 h at room temperature and then washed 4 times with 0.1% BSA in PBS. 50 μl of O-phenylenediamine solution (1 μg/ml O-phenylenediamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The $IC_{50}$ value was defined as the concentration of the test compound corresponding to half-maximal reduction in 450 nm absorbance.

| CPD # | $IC_{50}$, nM | CPD # | $IC_{50}$, nM |
|---|---|---|---|
| 2 | 0.46 | 106 | 1100 |
| 5 | 0.12 | 108 | 8830 |
| 9 | 0.3 | 112 | 241 |

Example 22

Inhibition of LPS-Induced TNF-α Production In Mice . . . In Vivo Assay

The ability of the compounds of this invention to inhibit the TNF-α release, in vivo, was determined using a minor modification of the methods described in described in Zanetti, G.; Heumann, D., et. al., "Cytokine production after intravenous or peritoneal Gram-negative bacterial challenge in mice," *J. Immunol.*, 148, 1890, (1992) and Sekut, L., Menius, J. A., et. al., "Evaluation of the significance of elevated levels of systemic and localized tumor necrosis factor in different animal models of inflammation," *J. Lab. Clin. Med.*, 124, 813, (1994).

Female BALB/c mice weighing 18–21 grams (Charles River, Hollister, Calif.) were acclimated for one week. Groups containing 8 mice each were dosed orally either with the test compounds dissolved in an aqueous vehicle containing 0.9% sodium chloride, 0.5% sodium carboxymethyl-cellulose, 0.4% polysorbate 80,0.9% benzyl alcohol (CMC vehicle) or only vehicle (control group). After 30 min., the mice were injected intraperitoneally with 20 μg of LPS (Sigma, St. Louis, Mo.). After 1.5 h, the mice were sacrificed by $CO_2$ inhalation and blood was harvested by cardiocentesis. Blood was clarified by centrifugation at 15,600×g for 5 min., and sera were transferred to clean tubes and frozen at −20° C. until analyzed for TNF-α by ELISA assay (Biosource International, Camarillo, Calif.) following the manufacturer's protocol.

The TNF-α inhibitory activity of test materials, i.e., the measure of the TNF-α content in the test group relative to the vehicle treated group (control group) at 30 mg was:

| CPD # | % Inhibition |
|---|---|
| 2 | 75% |
| 3 | 56% |
| 6 | 68% |
| 101 | 86 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound selected from the group of compounds represented by Formula (I):

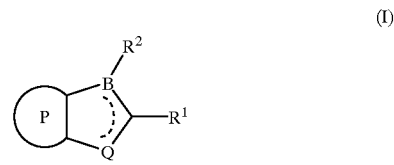

(I)

wherein:

$R^1$ is heteroaryl;

- - - - - - represents a bond between either B and $CR^1$ or Q and $CR^1$ such that:

(i) when - - - - - - is between Q and —$CR^1$— then:
  B is nitrogen;
  $R^2$ is aryl; and
  Q is —CR— wherein:
    R is hydrogen, alkyl, haloalkyl, cycloalkyl, cycloalkylalkyl, heteroalkyl, acyl, heterocyclyl, heterocyclylalkyl, heterocyclylcarbonyl, nitro, cyano, amino, monosubstituted amino, disubstituted amino, acylamino, sulfonylamino, —$OR^5$ (where $R^5$ is hydrogen, alkyl, heteroalkyl or heterocyclylalkyl), —$COOR^7$ (where $R^7$ is hydrogen or alkyl) or —CONR'R" (where R' and R" independently represent hydrogen, alkyl or heteroalkyl); and (ii) when - - - - - - is between B and —$CR^1$— then:
  B is carbon;
  $R^2$ is aryl or heteroaryl; and
  Q is —$NR^4$—, wherein:
    $R^4$ is hydrogen, alkyl, alkenyl, alkynyl, haloalkyl, cycloalkyl, cycloalkylalkyl, heteroalkyl, acyl, aralkyl, heteroaralkyl, heterocyclyl, heterocyclylalkyl, heterocyclylcarbonyl, —$OR^5$ (where $R^5$ is hydrogen, alkyl, heteroalkyl or heterocyclylalkyl), —$SO_2R"$ (where R" is alkyl, amino, monosubstituted amino or disubstituted amino), —CONR'R" (where R' and R" independently represent hydrogen, alkyl or heteroalkyl), -(alkylene)-Z or -(alkylene)-CO-(alkylene)-Z wherein:
      Z is cyano;
      —$COOR^7$ where $R^7$ is hydrogen or alkyl;
      —$CONR^8R^9$ where $R^8$ is hydrogen or alkyl, $R^9$ is alkoxy or -(alkylene)-$COOR^7$, or $R^8$ and $R^9$ together with the nitrogen atom to which they are attached form a heterocycle;
      —C(=$NR^{10}$)($NR^{11}R^{12}$) where $R^{10}$, $R^{11}$ and $R^{12}$ independently represent hydrogen or alkyl, or $R^{10}$ and $R^{11}$ together are —$(CH_2)_n$— where n is 2 or 3 and $R^{12}$ is hydrogen or alkyl; or —$COR^{13}$ where $R^{13}$ is alkyl, heteroalkyl, heterocyclylalkyl, aryl, aralkyl, heteroaryl or heteroaralkyl; and

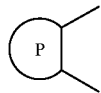

is a group represented by formula (S);

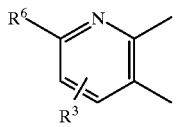
(S)

where:

$R^6$ is hydrogen, alkyl, heteroalkyl, heterocyclylalkyl, halo, cyano, nitro, amino, monosubstituted amino, disubstituted amino, —$COOR^{14}$, -(alkylene)-$COOR^{14}$ (where $R^{14}$ is hydrogen or alkyl), —$CONR^{15}R^{16}$ (where $R^{15}$ and $R^{16}$ independently represent hydrogen or alkyl, or $R^{15}$ and $R^{16}$ together with the nitrogen atom to which they are attached form a heterocycle), —$S(O)_nR^{17}$ (where n is an integer from 0 to 2 and $R^{17}$ is alkyl, amino, monosubstituted amino or disubstituted amino), —$OR^{18}$ (where $R^{18}$ is hydrogen, alkyl, heteroalkyl or heterocyclylalkyl), —NRC(O)R" [where R is hydrogen, alkyl or hydroxyalkyl and R" is hydrogen, alkyl, cycloalkyl or -(alkylene)-X where X is hydroxy, alkoxy, amino, alkylamino, dialkylamino, heterocyclyl or —$S(O)_nR'$ (where n is 0 to 2 and R' is alkyl)], —$NRSO_2R"$ [where R is hydrogen or alkyl and R" is alkyl or -(alkylene)-X where X is hydroxy, alkoxy, amino, alkylamino, dialkylamino or —$S(O)_nR'$ (where n is 0 to 2 and R' is alkyl)]; and $R^3$ is hydrogen, alkyl, alkenyl, alkynyl, haloalkyl, heteroalkyl, cycloalkyl, cycloalkylalkyl, cycloalkylthio, aralkyl, heteroaralkyl, heterocyclyl, heterocyclylalkyl, halo, cyano, nitro, amino, monosubstituted amino, disubstituted amino, acylamino, sulfonylamino, —$OR^{19}$ (where $R^{19}$ is hydrogen, alkyl, heteroalkyl or heterocyclylalkyl), —$COOR^{20}$ (where $R^{20}$ is hydrogen or alkyl), —$CONR^{21}R^{22}$ (where $R^{21}$ and $R^{22}$ independently represent hydrogen, alkyl or heteroalkyl, or $R^{21}$ and $R^{22}$ together with the nitrogen atom to which they are attached form a heterocycle), —$S(O)_nR^{23}$ (where n is an integer from 0 to 2 and $R^{23}$ is alkyl, heteroalkyl, amino, monosubstituted amino or disubstituted amino), -(alkylene)-Z" or -(alkylene)-CO-(alkylene)Z wherein:

Z" is cyano;
—$COOR^{24}$ where $R^{24}$ is hydrogen or alkyl;
—$CONR^{25}R^{26}$ where $R^{25}$ and $R^{26}$ independently represent hydrogen or alkyl, or $R^{25}$ and $R^{26}$ together with the nitrogen atom to which they are attached form a heterocycle;
—$C(=NR^{27})(NR^{28}R^{29})$ where $R^{27}$, $R^{28}$ and $R^{29}$ independently represent hydrogen or alkyl, or $R^{27}$ and $R^{28}$ together are —$(CH_2)_n$— where n is 2 or 3 and $R^{29}$ is hydrogen or alkyl; or
—$COR^{30}$ where $R^{30}$ is alkyl, heteroalkyl, heterocyclylalkyl, aryl, aralkyl, heteroaryl or heteroaralkyl; and their pharmaceutically acceptable salts, prodrugs, individual isomers, and mixtures of isomers, provided that both $R^3$ and $R^6$ are not either amino, monosubstituted amino or disubstituted amino.

2. The compound of claim 1 wherein, - - - - - - is between B and —$CR^1$—, and

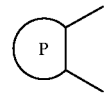

is a group represented by formula (S).

3. The compound of claim 2 wherein, $R^2$ is an aryl ring.

4. The compound of claim 3 wherein:

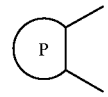

is a group represented by formula (S);

Q is —$NR^4$—;

$R^3$ is at the 7-position; and $R^6$ is hydrogen, alkyl, alkoxy or halo.

5. The compound of claim 4 wherein, $R^3$ is hydrogen, alkyl, halo or heteroalkyl.

6. The compound of claim 5 wherein, $R^1$ is a 4-pyridyl or 4-pyrimidinyl ring optionally substituted with a substituent selected from heteroalkyl, —NRR' (where R and R' are, independently of each other, hydrogen, alkyl, heterocyclylalkyl or heteroalkyl), —$NR^aC(O)R^b$ [where $R^a$ is hydrogen or alkyl and $R^b$ is hydrogen, alkyl or -(alkylene)-X where X is hydroxy, alkoxy, amino, alkylamino, dialkylamino, cycloalkyl, heterocyclyl, optionally substituted phenyl, imidazole or —$S(O)_nR'$ (where n is 0 to 2 and R' is alkyl)], —$NRSO_2R"$ [where R is hydrogen or alkyl and R" is alkyl or -(alkylene)-X where X is hydroxy, alkoxy, amino, alkylamino, dialkylamino or —$S(O)_nR'$ (where n is 0 to 2 and R' is alkyl)] or —OR (where R is alkyl or heteroalkyl).

7. The compound of claim 6 wherein, $R^2$ is a phenyl ring optionally substituted with one or two substituents selected from alkyl, halo or —OR where R is alkyl.

8. The compound of claim 7 wherein, $R^4$ is hydrogen, alkyl, cycloalkyl, heteroalkyl, acyl, heterocyclylalkyl, -(alkylene)-Z or -(alkylene)-CO-(alkylene)-Z wherein:

Z is —$COOR^7$ where $R^7$ is alkyl;

—$CONR^8R^9$ where $R^8$ is hydrogen or alkyl, $R^9$ is alkoxy or -(alkylene)-$COOR^7$, or $R^8$ and $R^9$ together with the nitrogen atom to which they are attached form a heterocycle; or —$C(=NR^{10})(NR^{11}R^{12})$ where $R^{10}$, $R^{11}$ and $R^{12}$ independently represent hydrogen or alkyl, or $R^{10}$ and $R^{11}$ together are —$(CH_2)_n$— where n is 2 or 3 and $R^{12}$ is hydrogen or alkyl.

9. The compound of claim 8 wherein:

$R^3$ is hydrogen, methyl, chloro, fluoro, 2-hydroxyethyl, 2-aminoethyl or 2-dimethylaminoethyl; and $R^6$ is hydrogen, methyl, methoxy, fluoro or chloro.

10. The compound of claim 9 wherein:

$R^1$ is a 4-pyridyl ring optionally substituted at the 2-position with a substituent selected from amino, methylamino, dimethylamino, acetylamino, methylsulfonylamino, 2-hydroxyethyl, 2-hydroxyethylamino, 3-hydroxypropylamino, 2-aminoethylamino, 2-aminoethyl, 3-aminopropyl, 2-dimethylaminoethyl, methoxy, 2-hydroxyethoxy or 2-dimethylaminoethoxy;

$R^2$ is a phenyl ring substituted with one or two substituents selected from methyl, fluoro, chloro or methoxy; and $R^3$ and $R^6$ are hydrogen.

11. The compound of claim 10 wherein, $R^4$ is hydrogen, methyl, ethyl, 2-hydroxyethyl, 3-hydroxypropyl, 2-aminoethyl, 3-aminopropyl, 2-methylaminoethyl, 3-methylaminopropyl, 2-dimethylaminoethyl, 3-dimethylaminopropyl, 2-(morpholin-4-yl)ethyl, 3-(morpholin-4-yl)propyl, 2-(piperidin-1-yl)ethyl, 3-(piperidin-1-yl)propyl, 2-(piperazin-1-yl)ethyl, or 3-(piperazin-1-yl)propyl.

12. The compound of claim 11 wherein:

$R^1$ is 2-(2-hydroxyethylamino)-4-pyridyl;

$R^2$ is 4-fluorophenyl; and $R^4$ is hydrogen; namely, 3-(4-fluorophenyl)-2-[2-(2-hydroxyethylamino)pyridin-4-yl]-1H-pyrrolo-[3,2-b]pyridine.

13. The compound of claim 11 wherein:

$R^1$ is 4-pyridyl;

$R^2$ is 4-fluorophenyl; and $R^4$ is 2-(morpholin-4-yl)ethyl;

namely, 3-(4-fluorophenyl)-1-[2-(morpholin-4-yl)ethyl]-2-(pyridin-4-yl)-1H-pyrrolo[3,2-b]pyridine.

14. The compound of claim 3 wherein:

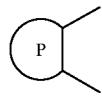

is a group represented by formula (S);

Q is —$NR^4$—; and $R^1$ is a heteroaryl ring substituted with —NRR' (where R is hydrogen, alkyl, or heteroalkyl and R' is heterocyclylalkyl or heteroalkyl).

15. The compound of claim 1 wherein, $R^3$ is at the 7-position;

$R^4$ is hydrogen, alkyl, cycloalkyl, heteroalkyl, acyl, heterocyclylalkyl, -(alkylene)-Z or -(alkylene)-CO-(alkylene)-Z wherein:

Z is —$COOR^7$ where $R^7$ is alkyd;

—$CONR^8R^9$ where $R^8$ is hydrogen or alkyl, $R^9$ is alkoxy or -(alkylene)-$COOR^7$, or $R^8$ and $R^9$ together with the nitrogen atom to which they are attached form a heterocycle; or —$C(=NR^{10})(NR^{11}R^{12})$ where $R^{10}$, $R^{11}$ and $R^{12}$ independently represent hydrogen or alkyl, or $R^{10}$ and $R^{11}$ together are —$(CH_2)_n$— where n is 2 or 3 and $R^{12}$ is hydrogen or alkyl; and $R^6$ is hydrogen, alkyl, alkoxy or halo.

16. The compound of claim 15 wherein:

$R^2$ is a phenyl ring optionally substituted with one or two substituents selected from alkyl, halo or —OR where R is alkyl;

$R^3$ is hydrogen, alkyl, halo or heteroalkyl; and $R^4$ is hydrogen, methyl, ethyl, 2-hydroxyethyl, 3-hydroxypropyl, 2-aminoethyl, 3-aminopropyl, 2-methylaminoethyl, 3-methylamino-propyl, 2-dimethylaminoethyl, 3-dimethylaminopropyl, 2-(morpholin-4-yl)ethyl, 3-(morpholin-4-yl)propyl, 2-(piperidin-1-yl)ethyl, 3-(piperidin-1-yl)propyl, 2-(piperazin-1-yl)ethyl, or 3-(piperazin-1-yl)propyl.

17. The compound of claim 16 wherein:

$R^1$ is a 4-pyridyl or 4-pyrimidinyl ring substituted with —NRR' (where R is hydrogen, alkyl, or heteroalkyl and R' is heterocyclylalkyl or heteroalkyl);

$R^2$ is a phenyl ring substituted with one or two substituents selected from alkyl, halo, or —OR where R is alkyl; and $R^3$ and $R^4$ are hydrogen.

18. The compound of claim 17 wherein:

the —NRR' substituent is at the 2-position of the 4-pyridyl or 4-pyrimidinyl ring and is 2-hydroxyethylamino, 2-aminoethylamino, 2-methylaminoethylamino or 2-dimethylaminoethylamino; and $R^2$ is a phenyl ring substituted with one or two substituents selected from methyl, fluoro, chloro or methoxy.

19. A pharmaceutical composition comprising a therapeutically effective amount of a compound of claim 1 and a pharmaceutically acceptable excipient.

20. A method of treatment of a disease in a mammal treatable by administration of a p38 MAP kinase inhibitor, comprising administration to the mammal a therapeutically effective amount of a compound of claim 1.

21. The method of claim 20, wherein the disease is an inflammatory disease.

* * * * *